United States Patent
Konishi et al.

(10) Patent No.: US 10,443,939 B2
(45) Date of Patent: Oct. 15, 2019

(54) EXHALATION MEASURING DEVICE AND METHOD FOR CONTROLLING EXHALATION MEASURING DEVICE

(71) Applicant: PHC HOLDINGS CORPORATION, Minato-ku, Tokyo (JP)

(72) Inventors: Takanori Konishi, Ehime (JP); Takeshi Oosora, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 446 days.

(21) Appl. No.: 15/123,251

(22) PCT Filed: Mar. 18, 2015

(86) PCT No.: PCT/JP2015/058103
§ 371 (c)(1),
(2) Date: Sep. 2, 2016

(87) PCT Pub. No.: WO2015/146751
PCT Pub. Date: Oct. 1, 2015

(65) Prior Publication Data
US 2017/0059245 A1    Mar. 2, 2017

(30) Foreign Application Priority Data

Mar. 26, 2014   (JP) ................. 2014-063305

(51) Int. Cl.
*F26B 21/12* (2006.01)
*F26B 21/00* (2006.01)
(Continued)

(52) U.S. Cl.
CPC ............. *F26B 21/12* (2013.01); *A61B 5/082* (2013.01); *A61B 5/097* (2013.01); *F26B 3/04* (2013.01);
(Continued)

(58) Field of Classification Search
CPC ...... A61B 2560/0242; A61B 2562/245; A61B 5/082; A61B 5/097; F26B 21/006;
(Continued)

(56) References Cited

U.S. PATENT DOCUMENTS 3,616,544 A  *  11/1971  Ottolenghi ............... F26B 3/00
                                                       34/341
4,194,298 A  *   3/1980  Hart ......................... F26B 5/16
                                                       34/331
(Continued)

FOREIGN PATENT DOCUMENTS

JP   2005-538819 A   12/2005
JP    2010-43915 A    2/2010
(Continued)

OTHER PUBLICATIONS

Search Report from the corresponding International Patent Application No. PCT/JP2015/058103 dated Jun. 16, 2015.
(Continued)

*Primary Examiner* — Kenneth Rinehart
*Assistant Examiner* — Logan P Jones
(74) *Attorney, Agent, or Firm* — McDermott Will & Emery LLP

(57) ABSTRACT

This exhalation measuring device is provided with a handle component, a chamber, a piezoelectric pump, and a drying mode controller. Exhalation is blown into the handle component. The chamber temporarily holds the exhalation that has been blown in. The piezoelectric pump supplies the exhalation held in the chamber to a measurement component. The dry mode controller executes a drying mode in which the piezoelectric pump is driven and outside air is drawn in from the handle component, after the measurement of exhalation by the measurement component.

11 Claims, 14 Drawing Sheets

(51) Int. Cl.
*F26B 3/04* (2006.01)
*G01N 25/56* (2006.01)
*A61B 5/097* (2006.01)
*A61B 5/08* (2006.01)
*G01N 33/497* (2006.01)

(52) U.S. Cl.
CPC .......... *F26B 21/006* (2013.01); *G01N 25/56* (2013.01); *G01N 33/497* (2013.01); *A61B 2560/0242* (2013.01); *A61B 2562/245* (2013.01); *G01N 2033/4975* (2013.01)

(58) Field of Classification Search
CPC ... F26B 21/12; F26B 3/04; G01N 2033/4975; G01N 25/56; G01N 33/497
See application file for complete search history.

(56) References Cited

U.S. PATENT DOCUMENTS

| | | | | |
|---|---|---|---|---|
| 4,270,564 | A * | 6/1981 | Blackburn | A61B 5/08 128/205.12 |
| 6,470,696 | B1 * | 10/2002 | Palfy | A42B 3/24 62/140 |
| 6,896,366 | B2 * | 5/2005 | Rice | A41D 13/1184 2/437 |
| 6,991,607 | B2 * | 1/2006 | Muz | A61B 5/0836 600/531 |
| 7,972,277 | B2 * | 7/2011 | Oki | A61B 5/097 600/529 |
| 8,814,804 | B2 * | 8/2014 | Walden | A61B 5/097 600/532 |
| 9,015,960 | B2 * | 4/2015 | Hopkin | F26B 9/02 34/417 |
| 9,931,058 | B2 * | 4/2018 | Hyohgo | A61B 5/087 |
| 10,016,149 | B2 * | 7/2018 | Yano | A61B 5/097 |
| 2004/0082872 | A1 * | 4/2004 | von Bahr | A61B 5/0803 600/532 |
| 2008/0066477 | A1 * | 3/2008 | Aoki | B60H 1/00785 62/150 |
| 2009/0275852 | A1 | 11/2009 | Oki et al. | |
| 2010/0095439 | A1 * | 4/2010 | Nolan | A42B 3/24 2/421 |
| 2011/0009764 | A1 * | 1/2011 | Lanier | A61B 5/0833 600/532 |
| 2015/0032019 | A1 * | 1/2015 | Acker | A61B 5/082 600/532 |
| 2015/0105684 | A1 | 4/2015 | Yang et al. | |

FOREIGN PATENT DOCUMENTS

| | | | |
|---|---|---|---|
| JP | 2010043915 A | * | 2/2010 |
| JP | 2011-153956 A | | 8/2011 |
| WO | 2004/023997 A1 | | 3/2004 |
| WO | 2009/057256 A1 | | 5/2009 |
| WO | 2013/003429 A1 | | 1/2013 |
| WO | 2013/161286 A1 | | 10/2013 |

OTHER PUBLICATIONS

Search Report from the corresponding European Patent Application No. 15769071.0 dated Feb. 28, 2017.

* cited by examiner

EXHALATION MEASURING DEVICE AND METHOD FOR CONTROLLING EXHALATION MEASURING DEVICE

PRIORITY

This is a National Stage Application under 35 U.S.C. § 365 of International Application PCT/JP2015/058103, with an international filing date of Mar. 18, 2015, which claims priority to Japanese Patent Application No. 2014-063305 filed on Mar. 26, 2014. The entire disclosures of International Application PCT/JP2015/058103 and Japanese Patent Application No. 2014-063305 are hereby incorporated herein by reference.

TECHNICAL FIELD

Certain implementations of the present invention relate to an exhalation measuring device and a method for controlling an exhalation measuring device, used, for example, in performing asthma detection, pulmonary function sensing, and so forth.

BACKGROUND

A conventional exhalation measuring device of this type comprised a handle component into which exhalation is blown, a chamber into which the exhalation is supplied from this handle component through a tube and temporarily held, a pump for supplying the exhalation held in this chamber to a measurement component, a controller for controlling the operation of this pump, and a display component that is connected to this controller.

Specifically, when an attempt to measure the nitrogen monoxide or the like contained in an exhalation is made by blowing exhalation directly into the measurement component, the state of the exhalation blown into the measurement component fluctuates, so the exhalation was first held in the chamber, and then the exhalation in this chamber was supplied by the pump to the measurement component.

SUMMARY

A problem with the conventional art discussed above was that the detection accuracy was low.

That is, since the exhalation blown in from the handle component is extremely high in humidity, if the outside air temperature is low, for example, condensation will occur inside the tube downstream from the handle component. As a result, the amount of exhalation supplied to the chamber is not consistent, and this results in lower detection accuracy.

In view of this, researchers have tried drying the condensation in the tube, for example, by installing a ventilation fan along the path traveled by the exhalation, and turning on a ventilation switch after exhalation measurement (see Patent Literature 2, for example).

However, if the user forgets to turn on the ventilation switch after exhalation measurement, the ventilation operation will not be executed by the ventilation fan, and as a result a large amount of condensation may remain in the tube, for instance, leading to diminished detection accuracy.

In view of this, and in light of the problems encountered with conventional exhalation measuring devices, it is an object of certain implementations of the present invention to provide an exhalation measuring device and a method for controlling an exhalation measuring device with which detection accuracy is improved.

To achieve this object, certain implementations of the present invention comprise a chamber, a pump, and a controller. The exhalation that is blown in is temporarily held in the chamber. The pump supplies the exhalation held in the chamber to a measurement component. The controller controls the operation of the pump. The controller also executes a drying mode in which the pump is driven and outside air is drawn in after measurement of the exhalation by the measurement component. This achieves the stated object of raising detection accuracy.

Specifically, with certain implementations of the present invention, the controller is configured to execute a drying mode in which the pump is driven and outside air is drawn in from the handle component, after the measurement of exhalation with the measurement component. Consequently, less condensation accumulates downstream from the handle component, and as a result the detection accuracy can be improved.

Certain implementations of present invention provide an exhalation measuring device and a method for controlling an exhalation measuring device with which detection accuracy is improved.

DETAILED DESCRIPTION

The exhalation measuring device in Embodiment 1 of the present invention will now be described through reference to the drawings.

Embodiment 1

1. Configuration
Overview of Exhalation Measuring Device

Figure 1:
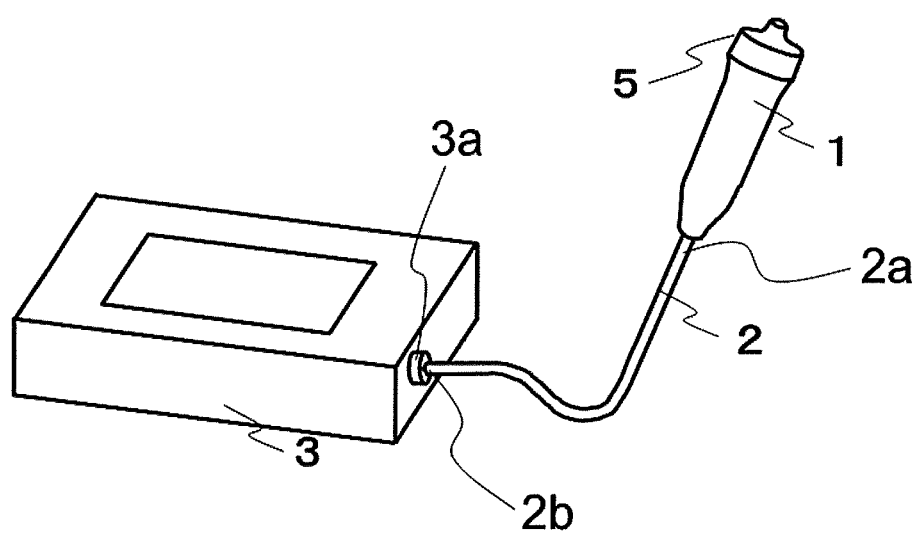
FIG. 1 is an oblique view of the exhalation measuring device in Embodiment 1 of the present invention.

FIG. 1 is an example of an exhalation measuring device, which measures the amount of nitrogen monoxide contained in exhalation, which is correlated to asthma detection.

As shown in FIG. 1, the exhalation measuring device in this embodiment comprises a handle component 1 and a measuring device main body 3 that is connected by a tube 2 to the handle component 1.

The handle component 1 is provided so that the user can blow in exhalation, and the user holds the handle component 1 while blowing in the exhalation. An end 2a of the tube 2 is connected to the handle component 1, and the measuring device main body 3, which is used to measure the exhalation that is blown in, is connected to the other end 2b of the tube 2. That is, the handle component 1 is connected to the measuring device main body 3 via the tube 2. A connector 3a (an example of an input component) to which the end 2b of the tube 2 is connected is provided to the measuring device main body 3. The exhalation that is blown in from the handle component 1 goes through the tube 2 and into the measuring device main body 3 from the connector 3a.
Handle Component 1

Figure 2:
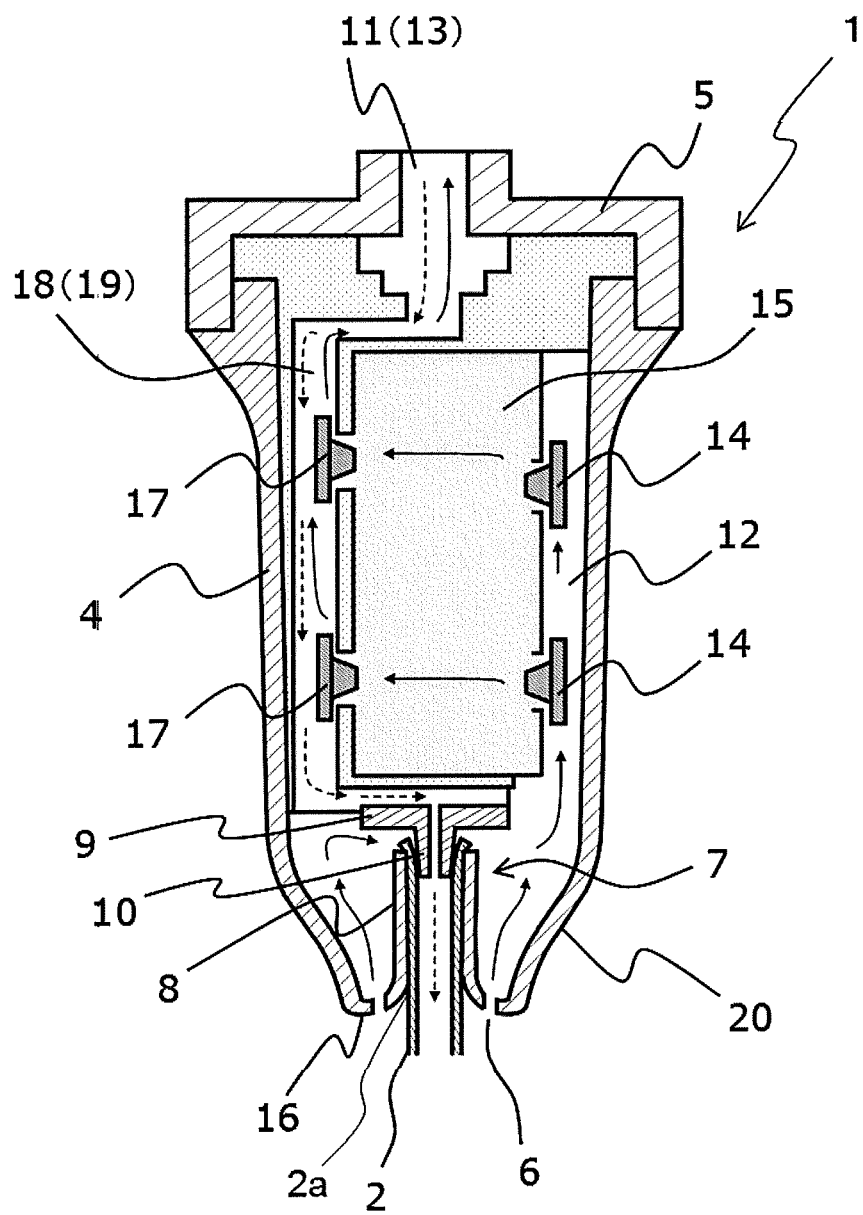
FIG. 2 is a cross section of the handle component of the exhalation measuring device in Embodiment 1 of the present invention.

FIG. 2 is a cross section of the handle component 1. As shown in FIG. 2, the handle component 1 is provided with a handle component main body 4, a mouthpiece 5 that is mounted above the handle component main body 4, inhalation holes 6 provided below the handle component main body 4, and a connector 7 that is connected to the end 2a of the tube 2.

This connector 7 is made up of a cylindrical part 8 of the handle component main body 4, and a connecting member 9 provided on the inside of the cylindrical part 8. A plurality of the inhalation holes 6 are formed in a ring shape around the cylindrical part 8.

The connecting member 9 has a small diameter part 10 whose diameter is smaller than that of the inner periphery of the cylindrical part 8.

The tube 2 is disposed between the outer peripheral face of the small diameter part 10 and the inner peripheral face of the cylindrical part 8. The tube 2 is fixed to the handle component main body 4 by squeezing the tube 2 between the small diameter part 10 and the cylindrical part 8.

The handle component main body 4 is further provided with a first inhalation channel 12 and a second inhalation channel 18 that connect the inhalation holes 6 with an inhalation inflow component 11 of the mouthpiece 5, and a discharge channel 19 that connects an exhalation discharge component 13 of the mouthpiece 5 with the end 2a of the tube 2. A filter 15 that removes from the air the component being measured by the exhalation measurement device of this embodiment (nitrogen monoxide in this embodiment) is provided between the first inhalation channel 12 and the second inhalation channel 18. A first one-way valve 14 is provided between the first inhalation channel 12 and the filter 15, and a second one-way valve 17 is provided between the filter 15 and the second inhalation channel 18. In Embodiment 1, the inhalation inflow component 11 and the exhalation discharge component 13 are formed at the same place, but may instead be provided separately.

The handle component 1 will be described here by going through the procedure by which the user measures exhalation.

First, in the state in FIG. 1, the user grasps the handle component main body 4 in FIG. 2 (part of the handle component 1) in order to blow into the handle component 1, and places his mouth against the exhalation discharge component 13 of the mouthpiece 5. The user then first inhales, with his mouth pressed against the exhalation discharge component 13, in order to be ready to blow exhalation into the measurement device main body 3.

When the user inhales, air is brought into the handle component 1 through the inhalation holes 6 of the handle component main body 4. The air that is brought in goes through the first inhalation channel 12, passes the first one-way valve 14, and flows into the filter 15.

Here, the inhalation holes 6 are formed on the side where the end 2a of the tube 2 is connected to the handle component main body 4, that is, to a curved face 16, so that the inhalation holes 6 will not be blocked off by the user's hand when the user holds the handle component main body 4 in his hand. The curved face 16 is formed in a tapered shape from the end 2a side of the tube 2 toward the other end 2b side, so that it widens from the cylindrical part 8 side to the outer peripheral part 20 side.

This configuration allows air to flow smoothly into the handle component 1, and results in a device that is more convenient to use, with no need for re-measurement or the like.

Next, the air that has flowed into the filter 15 has the nitrogen monoxide in it removed by a nitrogen monoxide remover disposed in the filter 15.

The air from which the nitrogen monoxide has been removed passes the second one-way valve 17, goes through the second inhalation channel 18, flows into the inhalation inflow component 11 of the mouthpiece 5, and is inhaled into the body of the user. After this, when the user exhales into the exhalation discharge component 13 of the mouthpiece 5, his exhalation flows into the discharge channel 19.

The exhalation that the user has blown in from the exhalation discharge component 13 of the mouthpiece 5 goes through the discharge channel 19, then through the tube 2 connected to the connector 7, and flows into the measurement device main body 3, where the nitrogen monoxide in the exhalation is measured.

The discharge channel 19 and the second inhalation channel 18 are formed at the same place, but may instead be provided separately.

Thus, the user holds the handle component 1 in his hand and blows into it, in the course of which the user pulls the handle component 1 into his mouth and blows his exhalation into it.
Measurement Device Main Body 3

Figure 3:
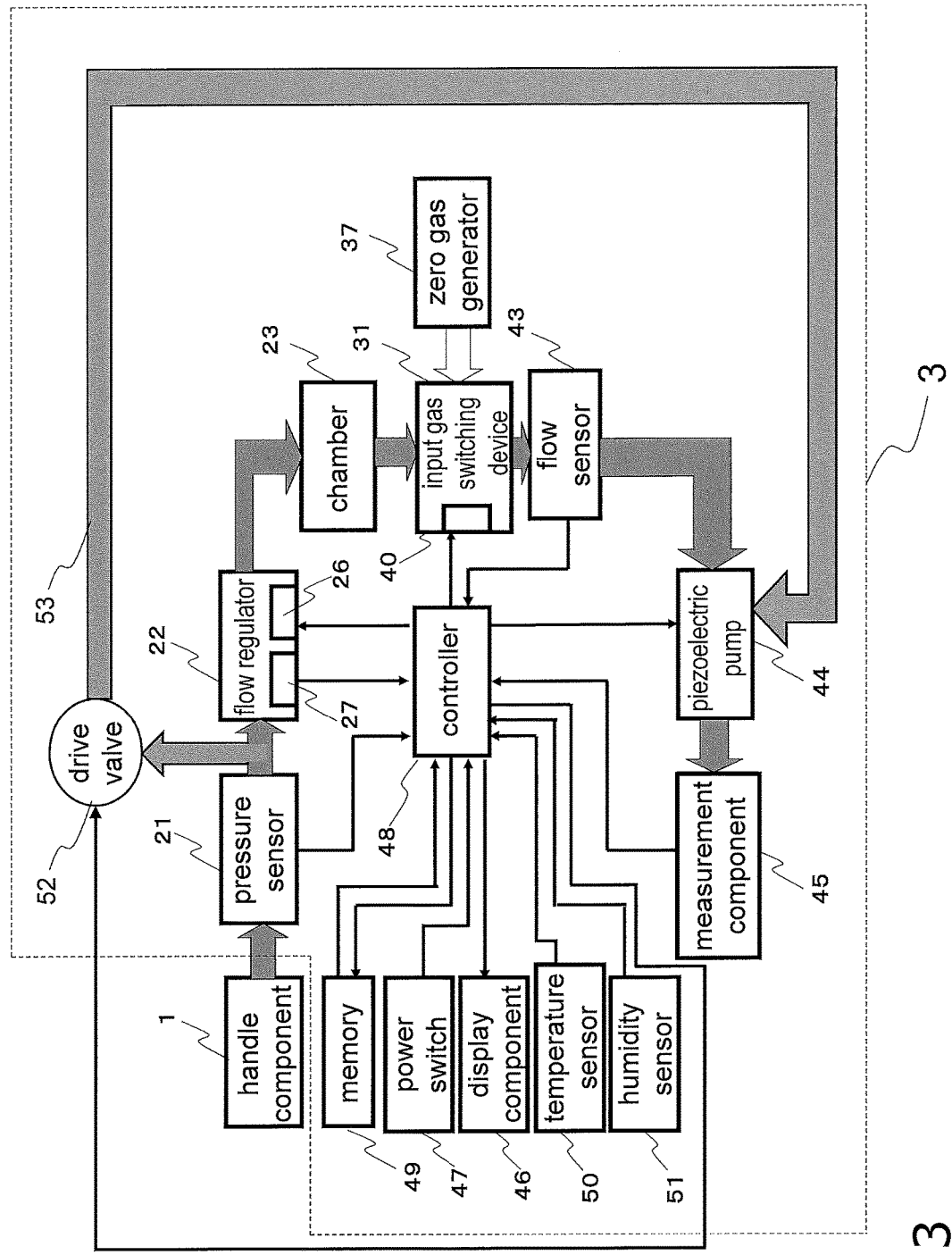
FIG. 3 is a control block diagram of the exhalation measuring device in Embodiment 1 of the present invention.

FIG. 3 is a block diagram of the configuration of the exhalation measurement device in this embodiment. As shown in FIG. 3, the measurement device main body 3 in this embodiment comprises a pressure sensor 21, a flow adjuster 22, a chamber 23, a zero gas generator 37, an input gas switching device 31, a flow sensor 43, a piezoelectric pump 44, a measurement component 45, a display component 46, a power switch 47, a memory 49, and a controller 48.
Pressure Sensor 21 and Flow Adjuster 22

The pressure sensor 21 measures the pressure of exhalation that flows from the handle component 1 into the measurement device main body 3 via the tube 2, and whether or not exhalation has been blown in can be determined by the pressure sensor 21.

Figure 4:
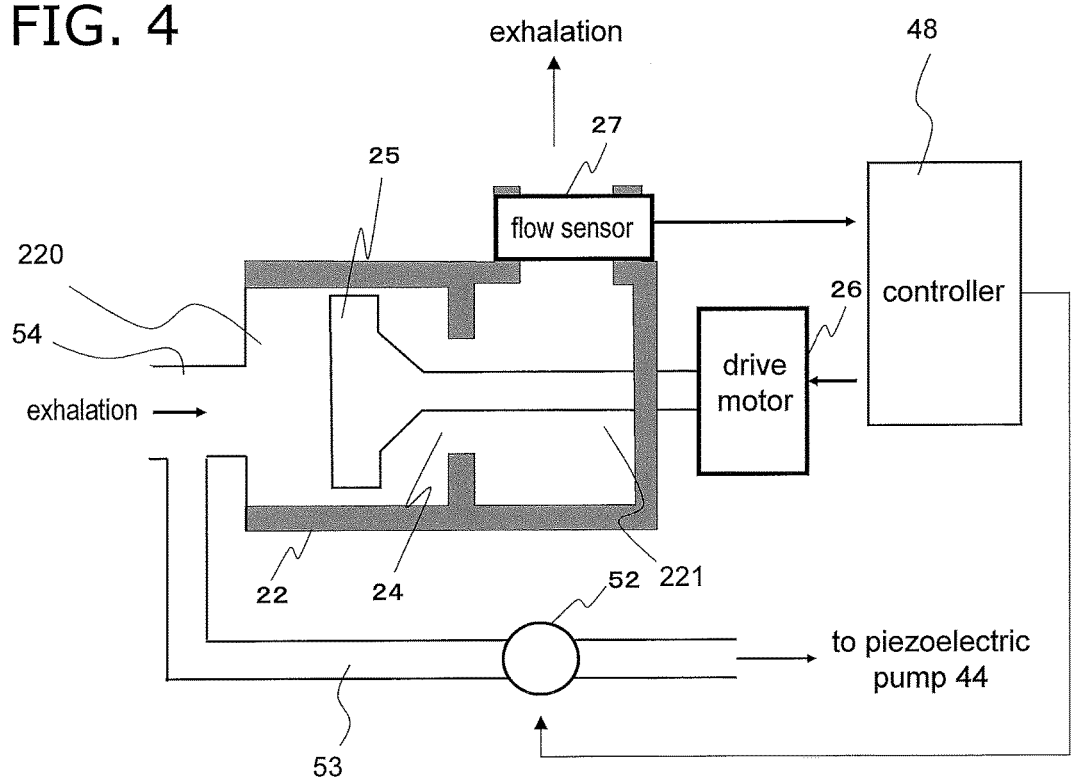
FIG. 4 is a cross section of a flow regulator in the exhalation measuring device in Embodiment 1 of the present invention.

FIG. 4 is a diagram of the configuration of the flow adjuster 22. The flow adjuster 22 adjusts the flow of the exhalation which flows in and supplies the exhalation to the chamber 23. The flow adjuster 22 has an exhalation inflow component 220 where the exhalation flows in, an exhalation outflow component 221 where the exhalation flows out, a valve hole 24 that allows the exhalation inflow component 220 to communicate with the exhalation outflow component 221, a drive valve 25 that can open and close the valve hole 24, a drive motor 26, and a flow sensor 27 provided on the outflow side to the chamber 23. The drive valve 25 is configured to be driven by the drive motor 26, and the flow sensor 27 monitors the exhalation quantity downstream of the flow adjuster 22. The drive motor 26 is controlled by the controller 48 on the basis of the sensing result by the pressure sensor 21 and the flow sensor 27.

Specifically, the exhalation supplied from the handle component 1, through the tube 2, to the measurement device main body 3 is then supplied to the chamber 23 in a state in which the flow has been adjusted by the pressure sensor 21 and the flow adjuster 22 shown in FIGS. 3 and 4.

More specifically, first the pressure sensor 21 senses the pressure of the exhalation, and detects the inflow of the exhalation. Then, the flow adjuster 22 reduces the aperture of the valve hole 24 with the drive valve 25 if the flow of exhalation sensed by the flow sensor 27 is large, and increases the aperture of the valve hole 24 with the drive valve 25 if the flow of exhalation sensed by the flow sensor 27 is small. This control stabilizes the flow of exhalation to the chamber 23.

Also, a bypass 53 that bypasses a chamber 23 (discussed below) is connected to the channel 54 connecting the pressure sensor 21 and the flow regulator 22. A drive valve 52 is disposed along the bypass 53, and the drive valve 52 is opened and closed by a drying mode controller 140.

Chamber 23

Figure 5:
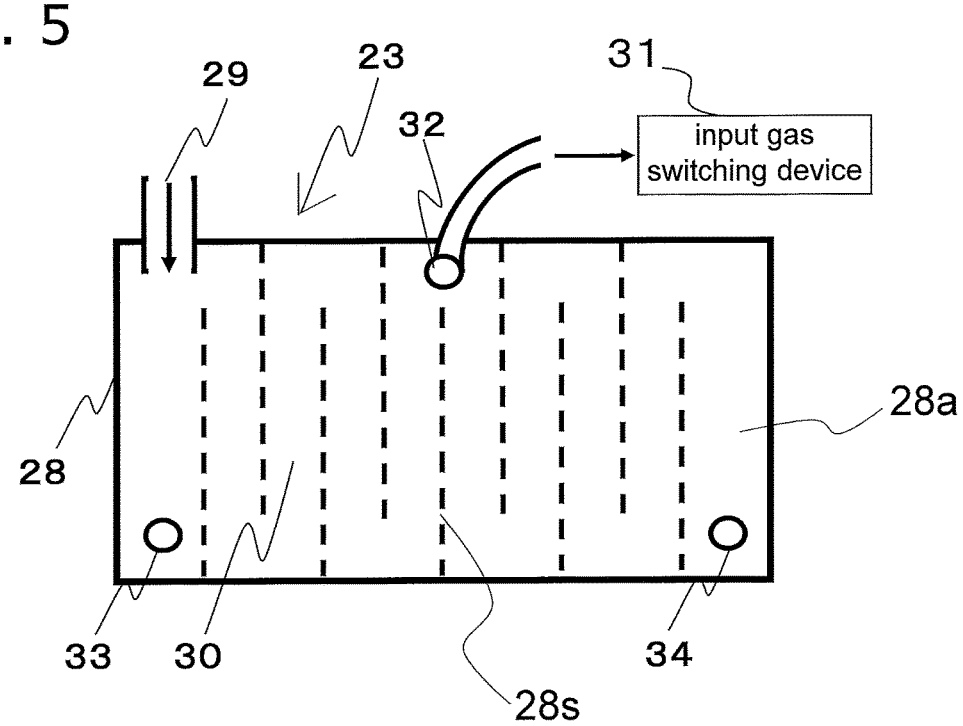
FIG. 5 is a cross section of the chamber of the exhalation measuring device in Embodiment 1 of the present invention.

As shown in FIG. 5, the chamber 23 is provided with an inflow opening 29 from the flow regulator 22 side on one end side of a container 28. An undulating path 30 is formed within this container 28, and an outflow opening 32 going to the input gas switching device 31 shown in FIG. 3 is formed in the middle portion of this undulating path 30. Intake/exhaust openings 33 and 34 are formed at the start and end sides of the undulating path 30.

The container 28 is substantially cuboid in shape, and two substantially rectangular opposing faces (the front and rear sides as seen in the drawings), and side faces that are provided between these and substantially perpendicular thereto.

The container 28 is installed on the inner face of the housing of the measuring device main body 3. In FIG. 5, one of the opposing faces of the container 28 is numbered 28*a*. The intake/exhaust openings 33 and 34 are formed by through-holes that pass through this face 28*a*. Walls 28*s* are formed substantially perpendicular to the face 28*a*, and the undulating path 30 is formed by these walls 28*s*.

The intake/exhaust openings 33 and 34 are linked to the outside of the measuring device main body 3, so the inside of the chamber 23 is always open to the atmosphere.

Input Gas Switching Device 31

Figure 6:
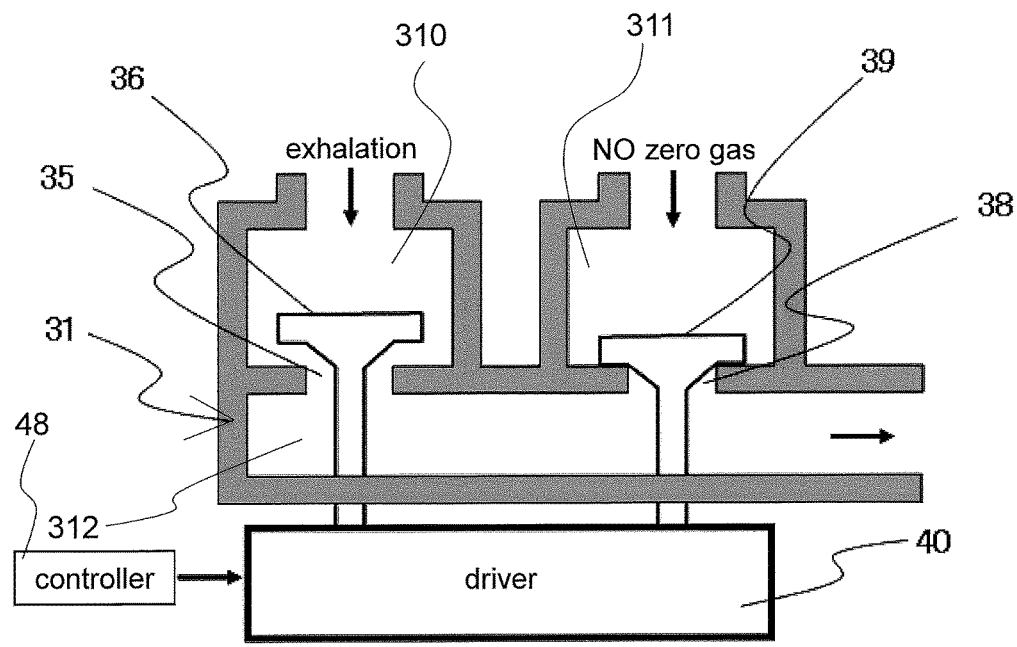
FIG. 6 is a cross section of an input gas switching device in the exhalation measuring device in Embodiment 1 of the present invention.

FIG. 6 is a simplified view of the configuration of the input gas switching device 31.

As shown in FIG. 6, the input gas switching device 31 has an exhalation inflow component 310, a zero gas inflow component 311, an outflow component 312, a valve hole 35, a drive valve 36, a valve hole 38, a drive valve 39, and a driver 40.

Exhalation flows into the exhalation inflow component 310 from the outlet 32 of the chamber 23. NO zero gas flows into the zero gas inflow component 311 from the zero gas generator 37 (discussed below). The zero gas or exhalation that has flowed in flows out from the outflow component 312 to the flow sensor 43 (discussed below) side.

The valve hole 35 allows the exhalation inflow component 310 to communicate with the outflow component 312. The drive valve 36 is able to open and close the valve hole 35, and is driven by the driver 40. The valve hole 38 allows the zero gas inflow component 311 to communicate with the outflow component 312. The drive valve 39 is able to open and close the valve hole 38, and is driven by the driver 40. The driver 40 is controlled by the controller 48, and drives the drive valve 36 and the drive valve 39.

Figure 7:
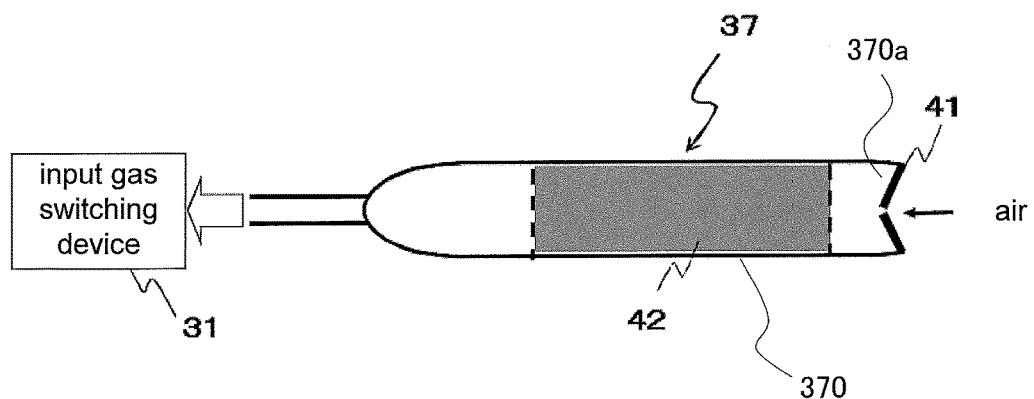
FIG. 7 is a cross section of a zero gas generator in the exhalation measuring device in Embodiment 1 of the present invention.

Specifically, the valve hole 35 and the drive valve 36 are disposed along the path by which exhalation is drawn out of the outflow opening 32 of the chamber 23, and the drive valve 36 and the drive valve 39 are disposed along the path by which air is drawn out of the zero gas generator 37 shown in FIG. 7. When the drive valve 36 and the drive valve 39 are driven by the driver 40, the exhalation in the chamber 23 or NO zero gas from the zero gas generator 37 can be selectively sent to the flow sensor 43 side.

Zero Gas Generator 37

FIG. 7 shows the configuration of the zero gas generator 37.

As shown in FIG. 7, the zero gas generator 37 has a container 370, a filter 42 disposed inside the container 370, and a one-way valve 41 disposed in an opening 370*a* at the opposite end of the container 370 from the input gas switching device 31. The one-way valve 41 opens only during inhalation. The filter 42 is provided downstream from the one-way valve 41 in the air intake direction and removes nitrogen monoxide.

Flow Sensor 43, Piezoelectric Pump 44, and Measurement Component 45

As shown in FIG. 3, the piezoelectric pump 44 is provided via the flow sensor 43 on the downstream side of the input gas switching device 31 shown in FIG. 6. The flow sensor 43 measures the flow of gas that is drawn in when the piezoelectric pump 44 is operated.

Figure 8A:
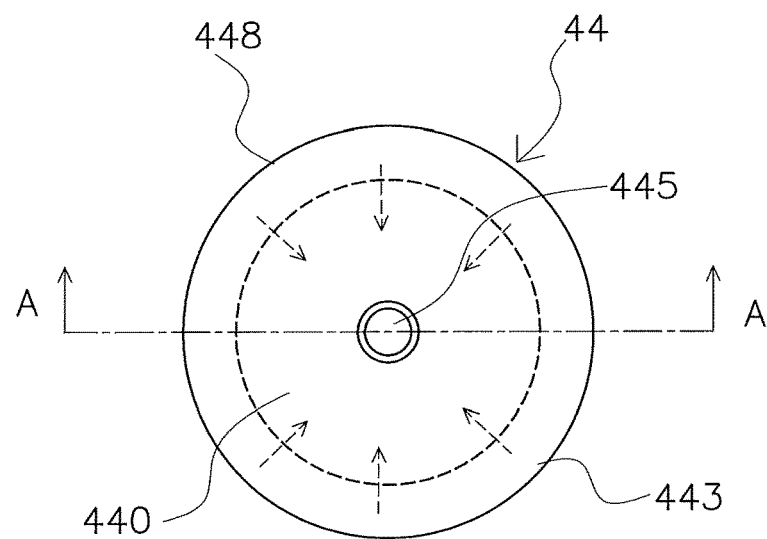
FIG. 8A is a simplified plan view of a piezoelectric pump in the exhalation measuring device in Embodiment 1 of the present invention.
Figure 8B:
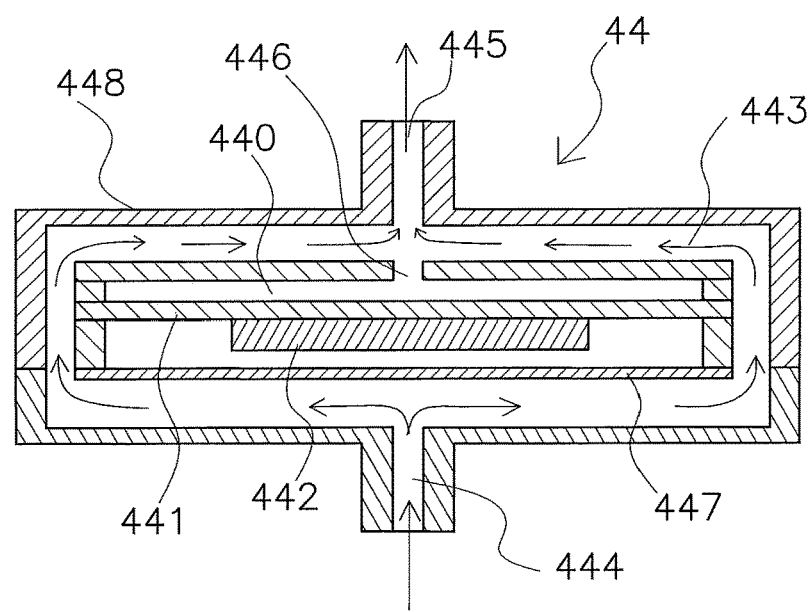
FIG. 8B is a cross section along the A-A line in FIG. 8A.

FIG. 8A is a simplified plan view of the piezoelectric pump 44. FIG. 8B is a cross section along the AA line in FIG. 8B. As shown in FIGS. 8A and 8B, the piezoelectric pump 44 has a substantially cylindrical housing 448. A gas outlet 445 is provided in the center of the upper face of the housing 448, and a gas inlet 444 is provided in the center of the bottom face of the housing 448. The inlet 444 is connected to the input gas switching device 31 via the flow sensor 43. The outlet 445 is connected to the measurement component 45.

The piezoelectric pump 44 also comprises a pump chamber 440 disposed in the center of the interior of the housing 448, a diaphragm 441 that forms part of the pump chamber 440 (the bottom face side), a piezoelectric element 442 provided on the lower side of the diaphragm 441 and the outside of the pump chamber 440, a cover 447 disposed so as to cover the piezoelectric element 442 from the lower side, and a channel 443 that is formed around the cover 447 and the pump chamber 440 and communicates with the pump chamber 440 via a hole 446. More precisely, the channel 443 is formed between the pump chamber 440 and the housing 448, and between the housing 448 and the cover 447, on the upper face side, the side face sides, and the lower face side of the cover 447 and the pump chamber 440.

The diaphragm 441 is vibrated by vibrations from the piezoelectric element 442, and gas moves through the channel 443 from the inlet 444 toward the outlet 445 as the pump chamber 440 increases or decreases in volume (see the arrows in FIGS. 8A and 8B).

With the piezoelectric pump 44, since the vibration of the piezoelectric element 442 provides a gas pumping function, vibration of the piezoelectric element 442 sends exhalation or zero gas into the measurement component 45. This will be discussed in detail below, but examples of parameters that are inputted in order to actuate the piezoelectric pump 44 include the vibration frequency, the applied voltage, and the duty ratio of the applied voltage at which the piezoelectric element 442 vibrates. The accuracy of the flow sent to the measurement component 45 can be improved, and measurement can be performed more accurately, by setting these parameters to the proper values. The control for obtaining the proper values for these parameters will be discussed below.

The measurement component 45 is provided downstream from the piezoelectric pump 44. With this measurement component 45, the amount of nitrogen monoxide is sensed and the result is displayed on the display component 46.

As shown in FIG. 3, the above-mentioned pressure sensor 21, drive motor 26, flow sensor 27, driver 40, flow sensor 43, piezoelectric pump 44, measurement component 45, display component 46, and power switch 47 are connected to the controller 48.

Controller 48

Figure 9:
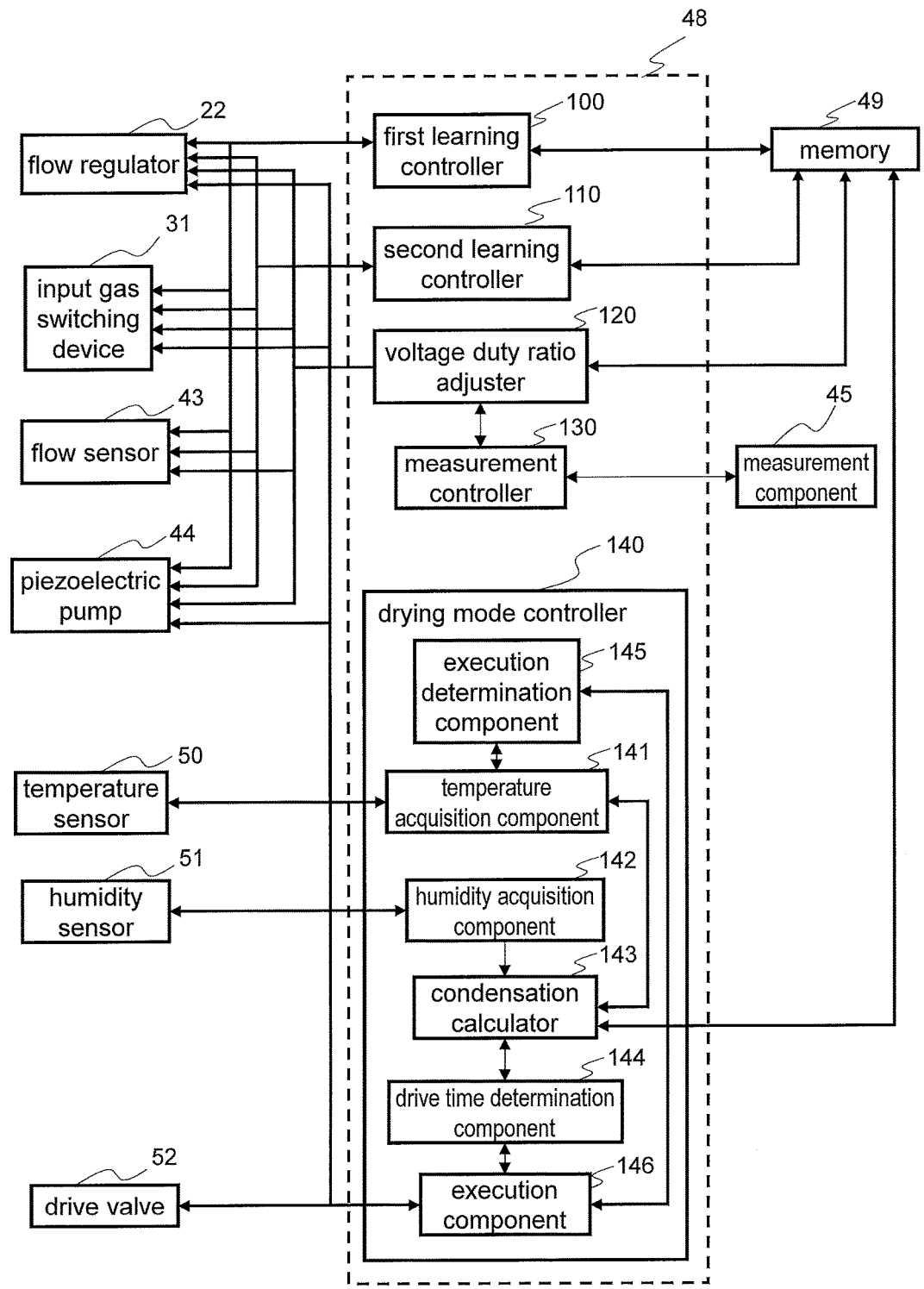
FIG. 9 is a control block diagram of the exhalation measuring device in Embodiment 1 of the present invention.

FIG. 9 is a block diagram of the configuration of the controller 48.

The controller 48 of the exhalation measuring device in this embodiment has a first learning controller 100, a second learning controller 110, a voltage duty ratio adjuster 120, a measurement controller 130, and the drying mode controller 140.

The first learning controller 100, the second learning controller 110, and the voltage duty ratio adjuster 120 select and set the vibration frequency, drive voltage, and duty ratio, which are parameters for operating the piezoelectric pump 44 in measuring nitrogen monoxide concentration with the measurement component 45. The measurement controller 130 performs measurement by controlling the measurement component 45 on the basis of the set parameters. The drying mode controller 140 executes a drying mode after measurement on the basis of temperature, humidity, and other such conditions.

First Learning Controller 100

The first learning controller 100 calculates the drive voltage and a first drive frequency at which the piezoelectric pump 44 is operated. The first learning controller 100 senses the resonance frequency of a piezoelectric element of the piezoelectric pump 44 by varying the frequency in a state in which a specific voltage has been applied. The first learning controller 100 then compares the flow sensed by the flow sensor 43 in the operation of the piezoelectric pump 44 using the above-mentioned specific values for voltage and resonance frequency, to a target flow. When the piezoelectric pump 44 is operated, a state results in which NO zero gas is sent by the input gas switching device 31 from the zero gas generator 37 to the piezoelectric pump 44. Furthermore, the first learning controller 100 adjusts the above-mentioned specific applied voltage value, on the basis of the comparison result, so that the flow sensed by the flow sensor 43 will be the target flow.

The first learning controller 100 sets the resonance frequency found above as a first drive frequency, sets the adjusted applied voltage as a drive applied voltage, and stores these values in the memory 49.

Second Learning Controller 110

The second learning controller 110 selects and sets the second drive frequency and the drive duty ratio on the basis of the first drive frequency and the drive applied voltage.

The second learning controller 110 selects the lowest duty ratio by detecting a change in the duty ratio by varying the first drive frequency at specific frequency intervals while holding the flow steady, and varying the duty ratio of the drive applied voltage, on the basis of the flow sensed by the flow sensor 43.

The second learning controller 110 sets the frequency at which the lowest duty ratio was selected as the second drive frequency, and sets the selected duty ratio as the drive duty ratio in the memory 49.

Voltage Duty Ratio Adjuster 120

After the second drive frequency, the drive applied voltage, and the drive duty ratio have been set, if the flow sensed by the flow sensor 43 is different from the target flow, the voltage duty ratio adjuster 120 adjusts the drive applied voltage and the drive duty ratio on the basis of the second drive frequency so that the sensed flow will become the target flow.

Specifically, in measurement, the voltage duty ratio adjuster 120 compares the flow of exhalation from the chamber 23 produced by the piezoelectric pump 44 operated using the second drive frequency, the drive applied voltage, and the drive duty ratio, and adjusts the applied voltage and the duty ratio so as to achieve the target flow. The voltage duty ratio adjuster 120 sets the adjusted drive applied voltage and drive duty ratio as the new drive applied voltage and drive duty ratio in the memory 49.

Measurement Controller 130

The measurement controller 130 controls the input gas switching device 31, the zero gas generator 37, the measurement component 45, and so on during measurement. More specifically, after the concentration of nitrogen monoxide in the exhalation in the chamber 23 has been measured by the measurement component 45, the input gas switching device 31 is switched to the zero gas generator 37 side, and the nitrogen monoxide concentration in the NO zero gas (blank value) is measured, after which the blank value is subtracted from the nitrogen monoxide concentration in the exhalation to calculate the nitrogen monoxide concentration.

Drying Mode Controller 140

The drying mode controller 140 has a temperature acquisition component 141, a humidity acquisition component 142, a condensation calculator 143, a drive time determination component 144, an execution determination component 145, and an execution component 146.

The temperature acquisition component 141 acquires temperature information from a temperature sensor 50 that measures the temperature of the outside air. The humidity acquisition component 142 acquires humidity information from a humidity sensor 51 that measures the humidity of the outside air.

The condensation calculator 143 calculates the amount of condensation on the basis of the acquired temperature and humidity. The drive time determination component 144 determines how long to drive the piezoelectric pump 44 from the calculated amount of condensation.

The execution determination component 145 compares the acquired temperature to a specific temperature (such as 30° C.), determines whether or not it is above the specific temperature, and if it is above the specific temperature, stops the execution of the drying mode.

If the acquired temperature is lower than the specific temperature, the execution component 146 controls the driver 40 of the input gas switching device 31 to close the valve holes 35 and 38 with the drive valves 36 and 39 and open the drive valve 52. The execution component 146 then drives the piezoelectric pump 44 for the drive time calculated by the drive time determination component 144, causes the exhalation blown in through the handle component 1 to bypass the chamber 23, and supplies the exhalation to the piezoelectric pump 44.

2. Operation

Figure 10:
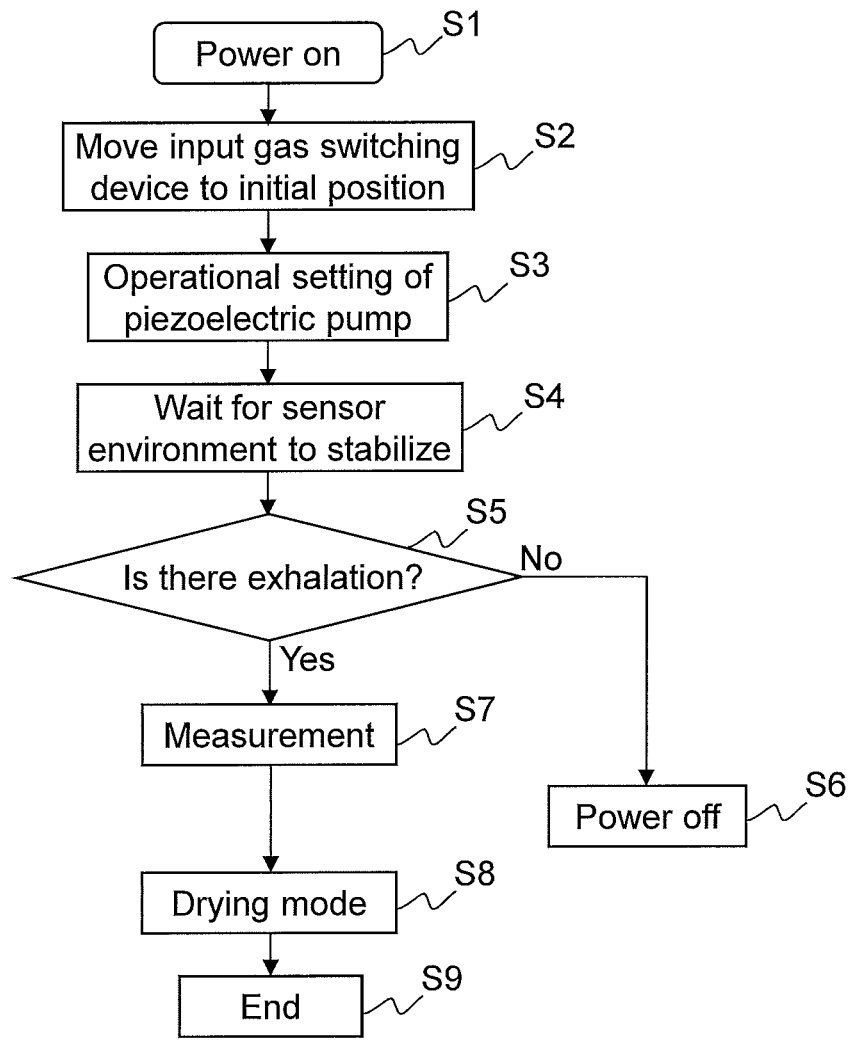
FIG. 10 is an operation flowchart of the exhalation measuring device in Embodiment 1 of the present invention.

FIG. 10 is a flowchart of the operation of the exhalation measuring device in this embodiment.

With the above configuration, to measure the exhalation, first the power switch 47 in FIG. 3 is turned on (S1 in FIG. 10). The controller 48 then puts the input gas switching device 31 shown in FIG. 6 in its initial state (S2 in FIG. 10).

This initial state is one in which the drive valves 36 and 39 are driven by the driver 40, the valve hole 35 is closed by the drive valve 36, and the valve hole 38 is open.

Next, the controller 48 performs operational setting (first operation setting mode) for the piezoelectric pump 44 (S3 in FIG. 10).

First Operation Setting Mode

Figure 11:
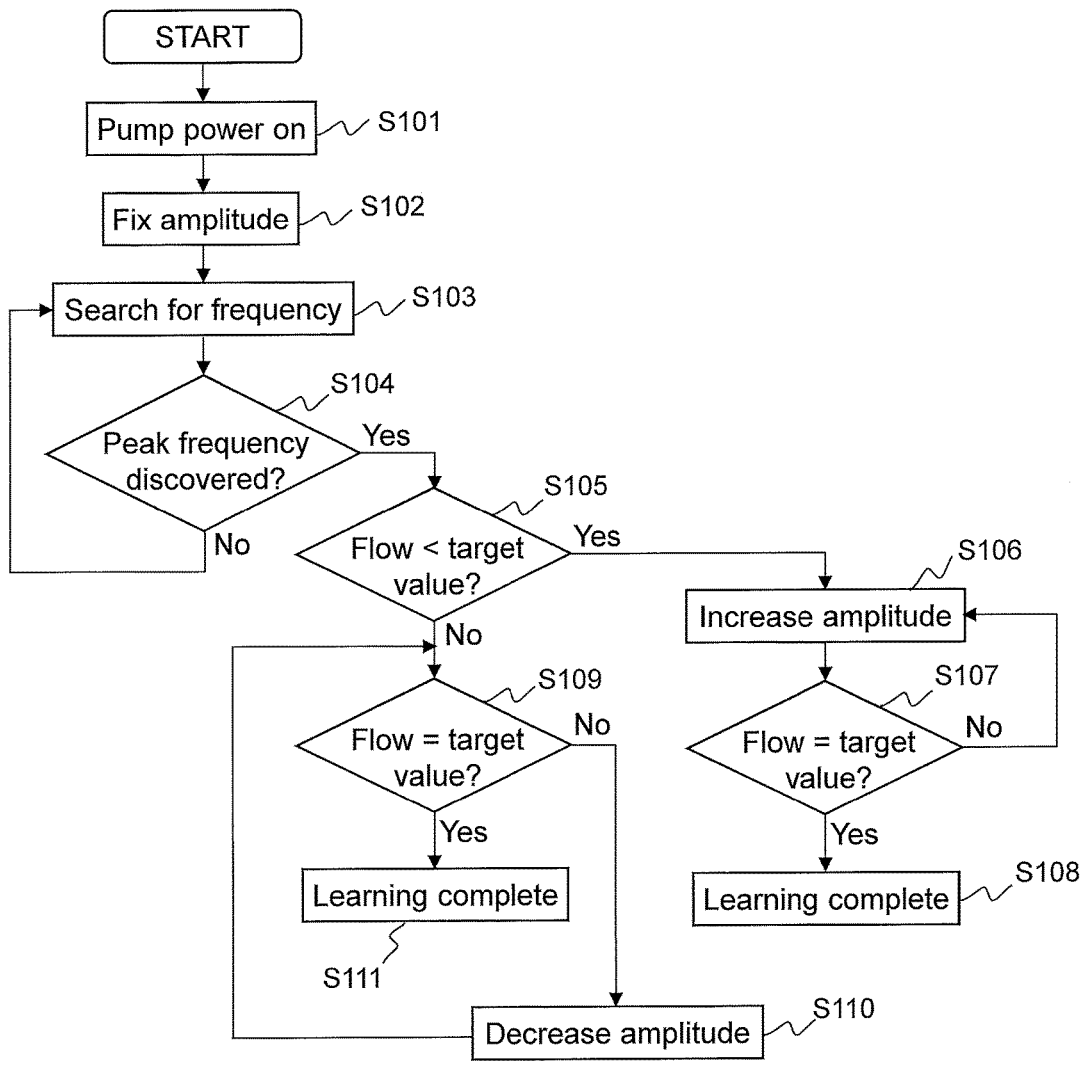
FIG. 11 is an operation flowchart of the exhalation measuring device in Embodiment 1 of the present invention.

The operational setting of the piezoelectric pump 44 will now be described in detail through reference to FIG. 11. FIG. 11 is a flowchart of the control of the operational setting of the piezoelectric pump 44 of the exhalation measuring device in this embodiment.

As is well know, the piezoelectric pump 44 itself is configured so that a piezoelectric element 442 is vibrated at 24 to 28 kHz, for example, and the exhalation is carried by this vibration force.

When this piezoelectric pump 44 is used, first the first learning controller 100 of the controller 48 turns on the piezoelectric pump 44 (S101 in FIG. 11), then sets the voltage applied to the piezoelectric element 442 to 6 V, for example (S102 in FIG. 11), and once the amplitude is fixed, performs a frequency search (S103 in FIG. 11).

In this frequency search, the above-mentioned 24 to 28 kHz and 6V are successively supplied at intervals of 256 Hz, for example, and the first learning controller 100 first performs a rough pre-selection of the frequency at which this piezoelectric element 442 resonates. Next, another 6 V is successively supplied at intervals finer than 256 Hz, such as intervals of 20 Hz, over a range of 256 Hz above and below this rough pre-selected frequency, and the frequency at which this piezoelectric element 442 resonates is selected.

Once the frequency at which the piezoelectric element resonates can be selected by this frequency search (S104 in FIG. 11), the first learning controller 100 then uses the flow sensor 43 to sense the flow. That is, since the valve hole 38 shown in FIG. 6 is open at this point, when the piezoelectric pump 44 is driven, air is drawn in by the piezoelectric pump 44 through the valve hole 38 and the one-way valve 41 of the zero gas generator 37, and the flow at this point is sensed by the flow sensor 43.

If the flow sensed by the flow sensor 43 is less than a target value of 3 mL/second, for example, the first learning controller 100 increases the voltage applied to the piezoelectric element from the above-mentioned 6 V (S105 and S106 in FIG. 11). After this, it is determined whether or not the flow sensed by the flow sensor 43 has reached the target value (S107 in FIG. 11).

When the flow sensed by the flow sensor 43 reaches the target value, the first learning controller 100 stores that applied voltage in the memory 49 shown in FIG. 3, along with the frequency (the first drive frequency) selected above in S104 in FIG. 11 (S107 and S108 in FIG. 11).

Meanwhile, in S105 in FIG. 11, if the flow is not less than the target value, the first learning controller 100 again determines whether or not the flow and the target value are the same. If the flow and the target value are different, the first learning controller 100 reduces the voltage applied to the piezoelectric element 442 from the above-mentioned 6 V (S109 and S110 in FIG. 11). Also, in S109 in FIG. 11, if the flow and the target value are the same, the first learning controller 100 stores this applied voltage in the memory 49 shown in FIG. 3, along with the frequency (the first drive frequency) selected above in S104 in FIG. 11 (S109 and S111 in FIG. 11).

The operational setting (S3) of the piezoelectric pump 44 in FIG. 10 is performed as above.

As discussed above, the frequency (the first drive frequency) and the applied voltage (drive applied voltage) are set in the operational setting S3. As to the duty ratio of the applied voltage, it is set to 50%, and is set to the same value as the initial duty ratio in the operational setting of the piezoelectric pump in S205 (discussed below).

Next, measurement preparations are completed by going through a sensor environment stabilization period (one to two minutes), indicated by S4 in FIG. 10. More specifically, the controller 48 causes the display component 46 to display a message prompting the user to blow into the device (S4 in FIG. 10).

Then, after a display prompting the user to blow into the device is given on the display component 46, the controller 48 detects whether or not the pressure sensor 21 has sensed the pressure within the past three minutes, for example. That is, if the user has not blown into the mouthpiece 5 within the past three minutes, the pressure sensor 21 does not sense the pressure, and as a result the power is switched off (S5 and S6 in FIG. 10).

If the user has blown into the mouthpiece 5 within the past three minutes, the pressure sensor 21 senses the pressure, and as a result an exhalation measurement operation is executed (S5 and S7 in FIG. 10).

Measurement Operation

The exhalation measurement operation (S7 in FIG. 10) will now be described through reference to FIG. 12.

Figure 12:
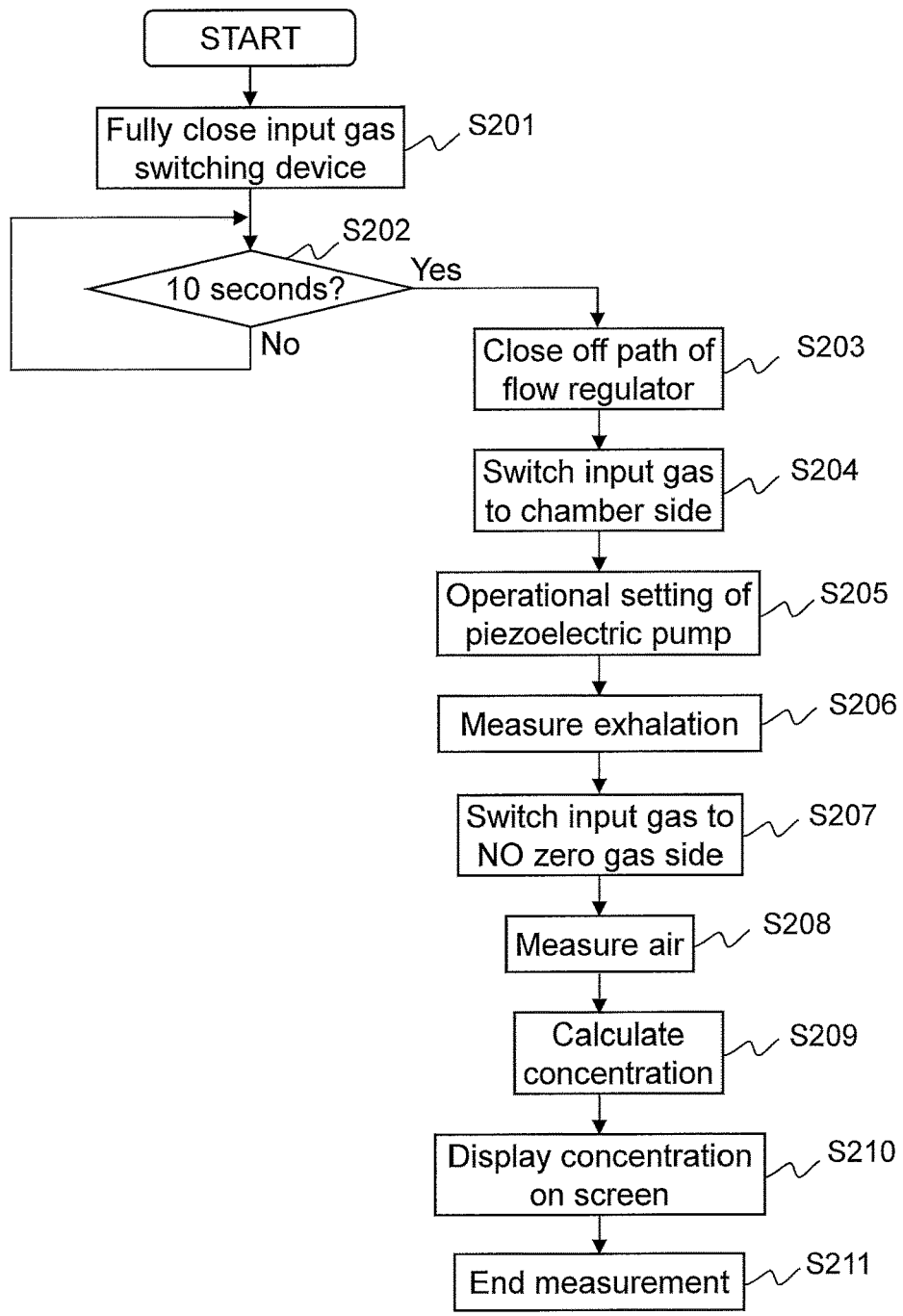
FIG. 12 is an operation flowchart of the exhalation measuring device in Embodiment 1 of the present invention.

During an exhalation measurement operation, the controller 48 first uses the driver 40 shown in FIG. 6 to drive the drive valves 36 and 39, thereby closing the valve holes 35 and 38 (S201 in FIG. 12).

This state is maintained for 10 seconds after the pressure is sensed by the pressure sensor 21 (S202 in FIG. 12).

During the 10 seconds for which this state is maintained, the flow of exhalation is sensed by the flow sensor 27 provided to the flow regulator 22, and the drive of the drive motor 26 is controlled on the basis of this. Under this control, exhalation is supplied to the chamber 23 at a steady flow through the flow regulator 22 (see FIG. 4). More specifically, in a state in which the flow has been confirmed by the flow sensor 27, the exhalation flows into the undulating path 30 through the inflow opening 29. Since the input gas switching device 31 is fully closed at this point as mentioned above, the outflow opening 32 of the chamber 23 is also closed, and part of the exhalation blown into the chamber 23 flows out through the intake/exhaust openings 33 and 34. That is, the air remaining in the chamber 23 is expelled by the exhalation that is blown in, and as a result the inside of the chamber 23 is filled with the exhalation.

Once 10 seconds have elapsed since the pressure was sensed by the pressure sensor 21, the controller 48 uses the drive valve 25 to close off the valve hole 24 of the flow regulator 22 (S203 in FIG. 12).

That is, the valve hole 24 is closed off by the drive valve 25 when the controller 48 drives the drive motor 26.

The controller 48 then drives the drive valve 36 with the driver 40 of the input gas switching device 31 to put the valve hole 35 in an open state (S204 in FIG. 12).

The valve hole 38 of the input gas switching device 31 is in a closed state at this point.

In this state, the second learning controller 110 of the controller 48 performs the operational setting of the piezoelectric pump 44 (second operational setting mode) (S205 in FIG. 12).

That is, the operational setting of the piezoelectric pump 44 was performed after the power switch 47 had been switched on as mentioned above (S3 in FIG. 10), but the operational setting of the piezoelectric pump 44 may be performed again in S205 in order to perform operational setting that is more accurate than in the first operational setting mode with progress of the time from it.

Second Operational Setting Mode

The operational setting of the piezoelectric pump 44 (second operational setting mode) will now be described through reference to FIG. 13.

More specifically, the power to the piezoelectric pump 44 has already been switched on (S101 in FIG. 11), and the voltage applied to the piezoelectric element has also been set to a suitable value (such as 6 V) during the operational setting in FIG. 11. Accordingly, the proper drive frequency is then set again by switching the frequency in units of 20 Hz.

Since the drive frequency has also already been set in FIG. 11 at this point, the second learning controller 110 again selects a frequency while varying the duty ratio on the basis of the following S301 to S316 within a range of 256 Hz above and below this frequency. Here, we will let the target flow at the time of measurement have a lower value than that used in FIG. 11, setting it to 2 mL/second, for example. The duty ratio of the voltage applied to the piezoelectric element 442 is then set to 50% of the maximum value during learning (S301 in FIG. 13).

Next, the second learning controller 110 uses the flow sensor 43 to sense the flow. Since the valve hole 35 shown in FIG. 6 is open at this point, when the piezoelectric pump 44 is driven, the exhalation in the chamber 23 is drawn into the piezoelectric pump 44 through the valve hole 35 of the input gas switching device 31 and the outflow opening 32, and the flow at this point is sensed by the flow sensor 43.

Figure 13:
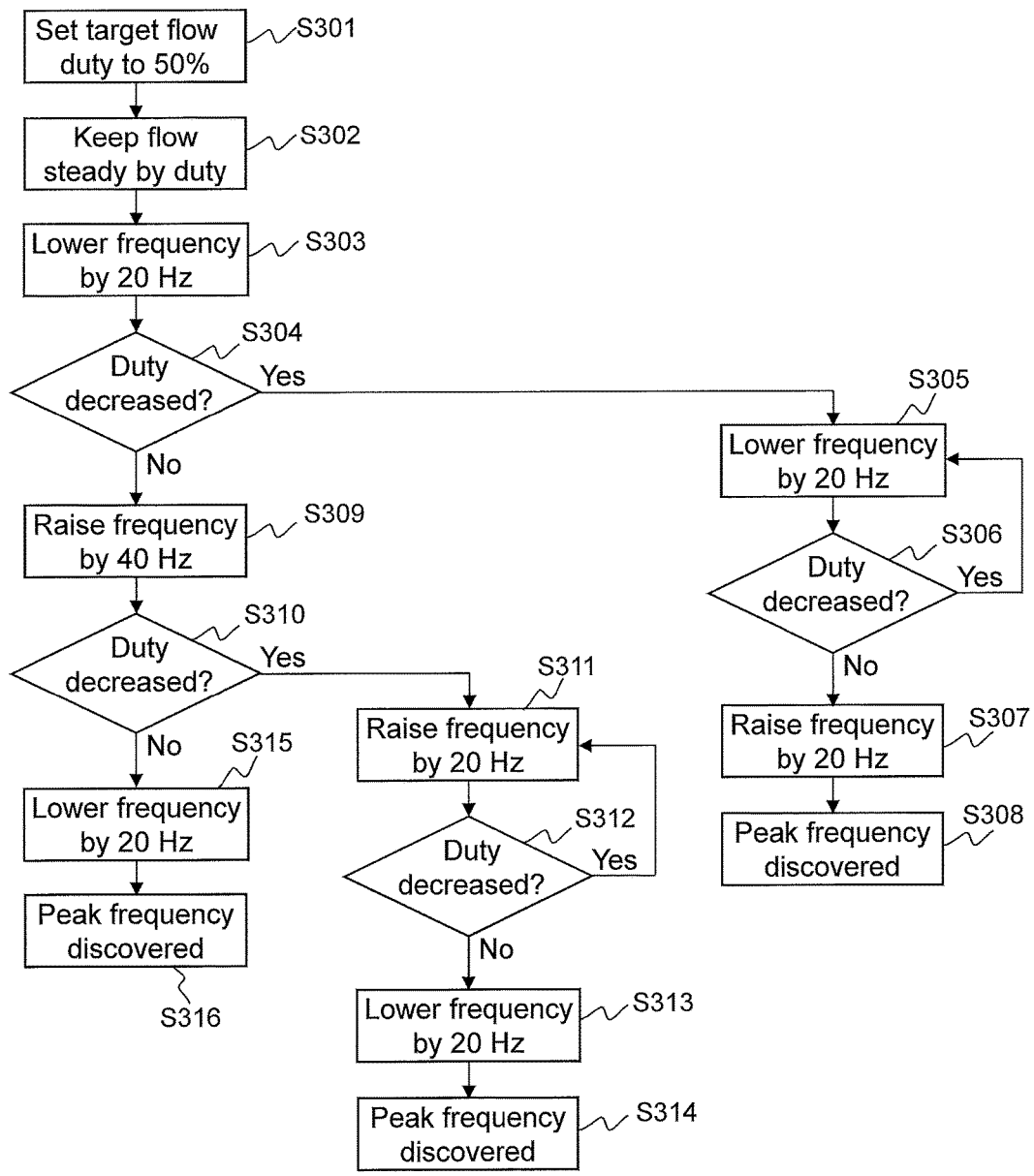
FIG. 13 is an operation flowchart of the exhalation measuring device in Embodiment 1 of the present invention.

The second learning controller 110 then changes the duty ratio and keeps the flow steady (S302 in FIG. 13). For example, if the flow is less than the target flow, the duty ratio is increased 1% at a time, and conversely, if the flow is greater than the target value, the duty ratio is reduced 1% at a time until the target flow is attained. In this state (a state in which the flow is held steady), if the frequency is changed by a constant amount (such as in units of 20 Hz) up or down from the frequency already set in FIG. 11, the duty ratio decreases as the peak frequency is approached. This fact is utilized to reset the peak frequency.

First, the second learning controller 110 reduces the frequency by 20 Hz from the already set frequency (S303 in FIG. 13), and determines whether the duty ratio has decreased (S304 in FIG. 13). If the duty ratio has decreased, the second learning controller 110 lowers the frequency another 20 Hz, determines whether the duty ratio has been reduced compared to the duty ratio before the change (this can also be called the duty ratio at a frequency of +20 Hz), and repeats this process (S305 and S306 in FIG. 13). The second learning controller 110 then detects that the frequency setting before the duty ratio did not come to reduce is the frequency at which the piezoelectric element 442 vibrates the most, and records the frequency before the duty ratio did not come to reduce in the memory 49 (FIG. 3) as the second drive frequency (S307 and S308 in FIG. 13).

Specifically, if the duty ratio after the frequency was changed by −20 Hz has not been reduced compared to the duty ratio at the frequency prior to the change, the second learning controller 110 selects the duty ratio at the frequency prior to the change as the lowest duty ratio when the frequency was changed by 20 Hz. The frequency at this lowest duty ratio is then recorded in the memory 49 as the frequency at which the piezoelectric element 442 vibrates the most.

If it is determined in S304 in FIG. 13 that the duty ratio was not reduced, the second learning controller 110 changes the current frequency by +40 Hz, that is, to a frequency that is 20 Hz higher than the frequency set in FIG. 11 (S309 in FIG. 13), and again determines whether or not the duty ratio was reduced (S310 in FIG. 13).

If the duty ratio was reduced in S310 in FIG. 13, the second learning controller 110 increases the frequency another 20 Hz, determines whether or not the duty ratio was reduced, and repeats this process (S311 and S312 in FIG. 13). The second learning controller 110 then detects that the frequency setting before the duty ratio did not come to reduce is the frequency at which the piezoelectric element 442 vibrates the most, and records it in the memory 49 (S313 and S314 in FIG. 13).

Specifically, if the duty ratio after the frequency was changed by +20 Hz has not been reduced compared to the duty ratio at the frequency prior to the change, the second learning controller 110 selects the duty ratio at the frequency prior to the change as the lowest duty ratio. The frequency (second drive frequency) at this lowest duty ratio is then recorded in the memory 49 as the frequency at which the piezoelectric element vibrates the most.

If it is determined in S310 in FIG. 13 that the duty ratio was not reduced, the second learning controller 110 detects the original frequency (the frequency obtained by subtracting 20 Hz from the frequency at which it was determined there was no reduction), that is, the frequency set in FIG. 11, is the frequency at which the piezoelectric element 442 vibrates the most, and records it in the memory 49 in FIG. 3 (S315 and S316 in FIG. 13).

The above-mentioned repetition of S305 and S306 in FIG. 13, or the repetition of S311 and S312 in FIG. 13, must fit within the time period discussed below, so the second learning controller 110 performs frequency setting within the range of ±256 Hz from the frequency set in FIG. 11. When the second learning controller 110 records the frequency at which the piezoelectric element 442 vibrates the most in the memory 49, the duty ratio at that frequency is also recorded.

As discussed above, the optimal drive frequency and the duty ratio at the optimal drive frequency are set as the operational setting of the piezoelectric pump 44.

Voltage Duty Ratio Control

Figure 14:
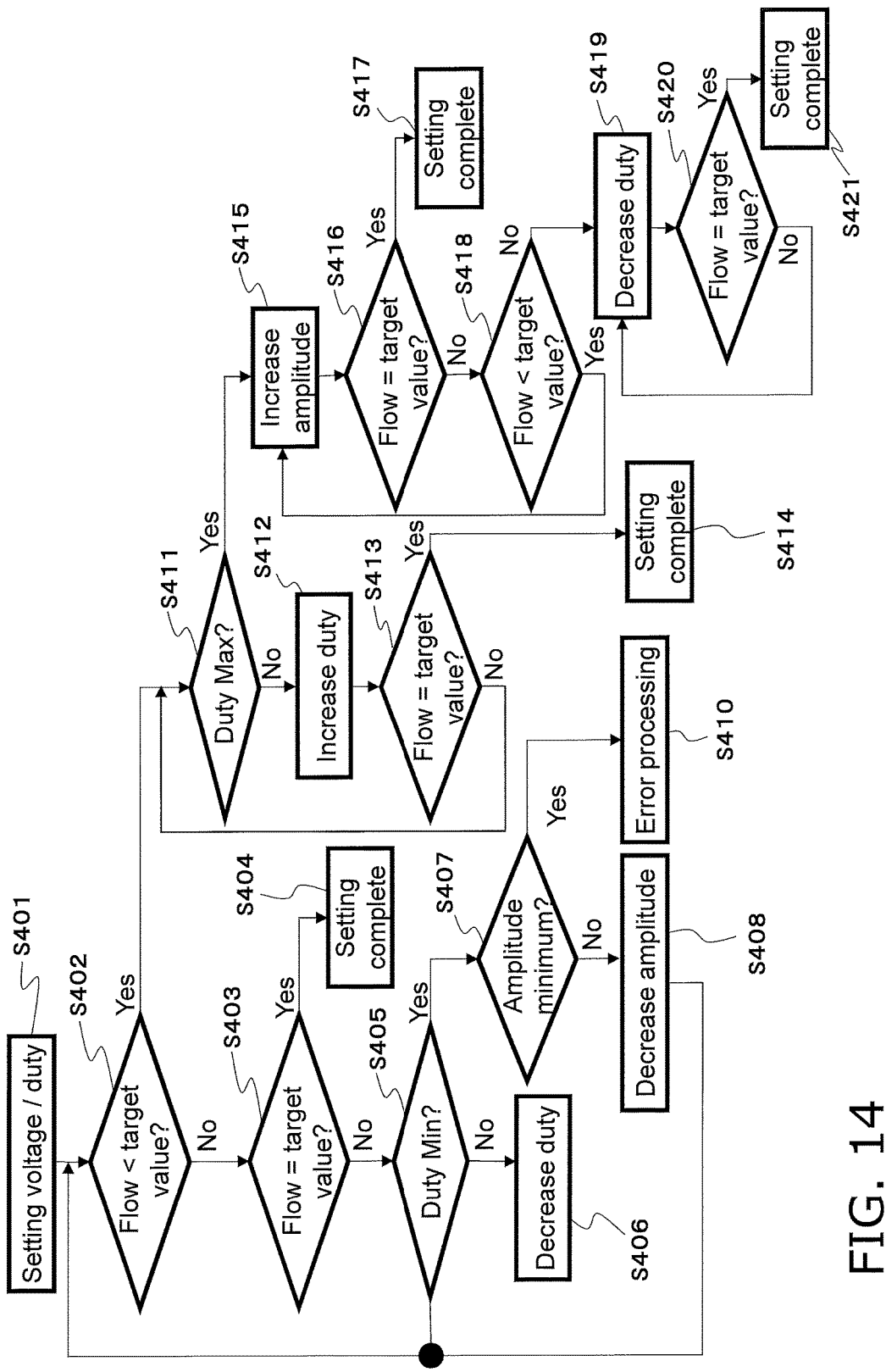
FIG. 14 is an operation flowchart of the exhalation measuring device in Embodiment 1 of the present invention.

Once the optimal drive frequency has been thus found as the operational setting, the voltage duty ratio adjuster 120 then performs voltage duty ratio control for setting the optimal drive voltage and the duty ratio thereof that keep the flow constant in the state of fixing this optimal drive frequency as shown in FIG. 14.

This voltage duty ratio control is executed by constantly monitoring the flow sensed by the flow sensor 43 during operation of the piezoelectric pump 44, even after the drive voltage and the duty ratio thereof have been set, and is performed to hold the flow steady even under the influence of disturbance caused by changes in the surrounding air flow, for example.

For instance, voltage duty ratio control is always executed when measuring exhalation in S206 after the operational setting of the piezoelectric pump has been executed in S205, and if the flow does not match the target flow, measurement is performed by the measurement component 45 after control is performed to adjust the drive applied voltage and the drive duty ratio so that the flow will match the target flow.

More specifically, in this control, the optimal voltage to be applied to the piezoelectric element 442 is found in the first operational setting mode, and the duty ratio is found in the second operational setting mode in FIG. 13, so first the controller 48 sets the voltage to be applied to the piezoelectric element 442 and the duty ratio to these values (S401 in FIG. 14).

Next, the voltage duty ratio adjuster 120 determines whether or not the flow sensed by the flow sensor 43 in this state is less than the target value, and if it is not less than the target value, it is then determined whether or not the flow is equal to the target value (S402 and S403 in FIG. 14).

Then, the setting is concluded if the flow is equal to the target value in S403 (S404 in FIG. 14). That is, the above-mentioned optimal frequency, drive voltage, and duty ratio are operationally set, and these values are recorded to the memory 49. In other words, the piezoelectric pump 44 is operated according to the drive applied voltage (amplitude) found in S3, and the second drive frequency and duty ratio found in S205.

In S403, if the flow is not equal to the target value, the voltage duty ratio adjuster 120 then determines in S405 whether or not the duty ratio of the drive voltage is the minimum value (10%) during use. If it has not gone under the minimum value (10%) during use, the duty is reduced by 1%, and control processing goes back to S402 (S406 and S402 in FIG. 14).

If it is determined in S405 that the duty has gone under the minimum value, the voltage duty ratio adjuster 120 then determines whether or not the value of the drive voltage is the minimum value (S407 in FIG. 14).

If the value of the drive voltage is not the minimum value, the voltage duty ratio adjuster 120 reduces the drive voltage by 0.1 V, and control processing goes back to S402 (S408 and S402 in FIG. 14). If the value of the drive voltage in S407 is the minimum value, the controller 48 causes the display component 46 to display an error message (S410 in FIG. 14).

That is, error processing is performed when the duty ratio of the drive voltage is at its minimum value, and the value of drive voltage is also at its minimum value.

In S402, if the flow sensed by the flow sensor 43 is less than the target value, in S411 the voltage duty ratio adjuster 120 determines whether or not the duty ratio of the drive voltage is the maximum value (40%) during use, and if it is not the maximum value, the duty ratio is increased by 1% (S412 in FIG. 14), and it is determined whether or not the flow sensed by the flow sensor 43 is equal to the target value (S413 in FIG. 14).

If the flow is equal to the target value, the setting is concluded (S414 in FIG. 14). That is, the above-mentioned optimal frequency (the second drive frequency), the optimal drive voltage, and the optimal duty are operationally set, and these values are stored in the memory 49 (S414 in FIG. 14). The setting range for duty ratio during use has a margin of 10% to both the upper and lower limits from the setting range of the duty ratio during learning, and is from 10% to 40%.

If the voltage duty ratio adjuster 120 determines in S411 that the duty ratio of the drive voltage is the maximum value during use, the voltage applied to the piezoelectric element 442 is increased by 0.1 V (S415 in FIG. 14).

Next, the voltage duty ratio adjuster 120 determines whether or not the flow sensed by the flow sensor 43 in this state is equal to the target value (S416 in FIG. 14).

If the flow is equal to the target value, setting is concluded (S417 in FIG. 14). That is, the above-mentioned optimal frequency (the second drive frequency), the optimal drive voltage, and the optimal duty are operationally set, and these values are stored in the memory 49 (S417 in FIG. 14).

In S416, if the flow is different from the target value, it is then determined whether or not the flow is less than the target value (S418 in FIG. 14), and if it is less, control processing goes back to S415.

In S418, if the flow is not less than the target value, the voltage duty ratio adjuster 120 reduces the duty ratio of the drive voltage by 1% (S419 in FIG. 14), and the voltage duty ratio adjuster 120 again determines whether or not the flow has reached the target value (S420 in FIG. 14).

In S420, if the flow is not equal to the target value, control processing goes back to S19. In S20, if the flow is equal to the target value, setting is concluded (S421 in FIG. 14). That is, the above-mentioned optimal frequency (the second drive frequency), the optimal drive voltage, and the optimal duty ratio are operationally set, and these values are stored in the memory 49 (S421 in FIG. 14).

The time it takes for the operational setting of the piezoelectric pump 44 to be performed as above (S205 in FIG. 12) is, for example, 10 seconds, but it actually takes 30 seconds for all of the exhalation in the chamber 23 to be supplied by the piezoelectric pump 44 to the measurement component 45. Therefore, the operational setting of the piezoelectric pump 44 (second operational setting mode) is concluded in the first 10 seconds of this 30-second period. The nitrogen monoxide concentration is then sensed from the exhalation supplied to the measurement component 45 during the few seconds after this operational setting (S206 in FIG. 12).

Once this measurement of the exhalation is concluded, the measurement controller 130 closes the valve hole 35 of the input gas switching device 31 with the drive valve 36, and the valve hole 38 is opened (S207 in FIG. 12).

In this state, the piezoelectric pump 44 then draws in air through the one-way valve 41 of the zero gas generator 37, the valve hole 38, and the filter 42 that removes nitrogen monoxide, and the nitrogen monoxide concentration of this air is measured by the measurement component 45 (S208 in FIG. 12).

Then, the measurement controller 130 calculates the final concentration of the exhalation from the nitrogen monoxide concentration of from the exhalation measured in S206 and the nitrogen monoxide concentration of the air measured in S208 (S209 in FIG. 12). The controller 48 causes the display component 46 to display this calculation result, and measurement is concluded (S210 and S211 in FIG. 12).

That is, the measurement in FIG. 10 (S7 in FIG. 10) is ended.

As shown in FIG. 5, the chamber 23 is provided with the intake/exhaust openings 33 and 34 on the upstream and downstream sides of the outflow opening 32 to the input gas switching device 31 in the undulating path 30, so when exhalation is blown in, there will be less gas flow resistance in the chamber 23. The gas flow resistance can also be reduced when the exhalation in the chamber 23 is supplied by the piezoelectric pump 44 to the measurement component 45.

Drying Mode

A feature of this embodiment is that the controller 48 shown in FIG. 3 executes a drying mode (S8 in FIG. 10) after this measurement (S7 in FIG. 10), after which the operation is ended (S9 in FIG. 10).

Specifically, as can be understood from FIG. 1, the tube 2 that connects the handle component 1 and the measuring device main body 3 is formed long enough to be convenient for the user. Furthermore, this tube 2 is exposed on the outside of the measuring device main body 3. Accordingly, there will be times when condensation forms inside the tube 2 when exhalation is blown in through the mouthpiece 5. There is the risk that this condensation will prevent the required amount of exhalation from being supplied into the chamber 23, and that as a result the measurement will not be performed properly.

To explain this further, the exhalation as a humidity of substantially 100% at 36 degrees, for example, just as with the human body temperature. If this exhalation is cooled by the outside air while moving through the tube 2, condensation can form inside the tube 2. Naturally, the amount of condensation that forms in a single measurement is very small, but a considerable amount can form when a number of measurements are made continuously. If a large amount of condensation forms, not only will it narrow the opening surface area in the tube 2, but the condensation may flow out and into the flow regulator 22 or the chamber 23. In view of this, in this embodiment control is performed so as to execute a drying mode (S8 in FIG. 10) whenever measurement is ended. If the drying mode is executed after each measurement, then just the tiny amount of condensation formed in the tube 2 as mentioned above will need to be removed, so condensation in the tube 2 can be kept to a minimum and be dried.

However, if the outside air environment to which the tube 2 is exposed is not low, there will be extremely little condensation formed in the tube 2, so ventilation may not need to be performed. In view of this, in this embodiment, as shown in FIGS. 3 and 9, the temperature sensor 50 that measures the outside air temperature and the humidity sensor 51 that measures the outside air humidity are connected to the drying mode controller 140 of the controller 48, and drying mode (S8 in FIG. 10) is executed on the basis of the measurement values from the temperature sensor 50 and the humidity sensor 51.

Figure 15:
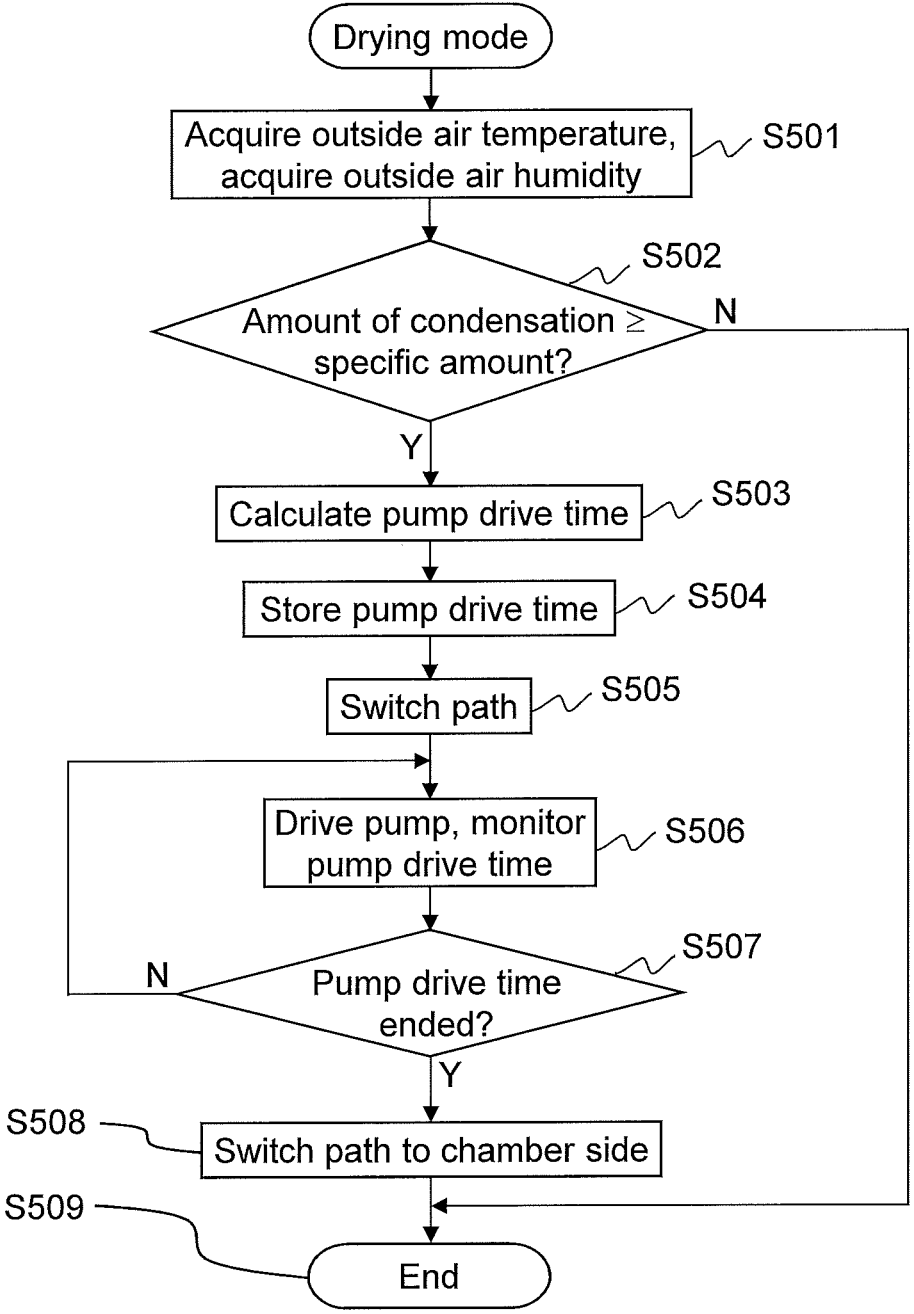
FIG. 15 is an operation flowchart of the exhalation measuring device in Embodiment 1 of the present invention.

FIG. 15 is a flowchart of the operation of the exhalation measuring device in drying mode in this embodiment.

More specifically, during execution of this drying mode, first the temperature acquisition component 141 of the drying mode controller 140 acquires the outside air temperature measured by the temperature sensor 50, and the humidity acquisition component 142 acquires the outside air humidity measured by the humidity sensor 51 (S501 in FIG. 15).

The execution determination component 145 then determines whether or not the amount of condensation is over a specific value, based on whether or not the outside air temperature is below a specific level (such as 30 degrees) (S502 in FIG. 15). If the outside air temperature is above a specific level (such as 30 degrees), control processing moves on to S509, and the drying mode is ended.

If the outside air temperature is above the specific level, this is a state in which condensation is unlikely to form, so even if the piezoelectric pump 44 is not driven to perform ventilation, any condensation will evaporate into the air touching the inside walls of the tube 2. Therefore, the condensation will diffuse outside of the handle component 1, and as a result there will be no accumulated increase in condensation inside the tube 2.

On the other hand, if the outside air temperature is low, the outer surface of the tube 2 exposed to the outside air will also be low, which will lower the temperature inside the tube 2, and as a result the above-mentioned exhalation (36 degrees and about 100% humidity, for example) will be cooled by the inner surface of the tube 2, and condensation will form there.

Since more condensation forms when the outside air temperature is low, the condensation calculator 143 calculates the amount of condensation from the outside air temperature, then the drive time determination component 144 calculates how long to operate the piezoelectric pump 44 to send outside air from the handle component 1 into the tube 2 in order to dry up this condensation.

The humidity measured by the humidity sensor 51 is also taken into account in this calculation. That is, if the humidity of the outside air flowing from the handle component 1 into the tube 2 is high (higher than 70%, for instance), it will be difficult to dry up the condensation formed on the inner surface of the tube 2. Accordingly, the drive time of the piezoelectric pump 44 that was set based on the above-mentioned outside air temperature must be increased (to 1.5 times, for instance). The drive time of the piezoelectric pump 44 is determined in this way (S503 in FIG. 15), and this drive time is stored in the memory 49 (S504 in FIG. 15).

The amount of condensation that forms will also be affected by how the exhalation is blown in, the shape of the constituent parts (such as the tube diameter), and so forth, so the relation between the outside air temperature and the amount of condensation formed may be found experimentally, and the amount of condensation may be calculated on the basis of the result.

Doing this allows the amount of condensation to be calculated more accurately than when the amount is calculated from the outside air temperature alone. The drying mode should be executed as discussed above if this condensation amount exceeds a specific value.

Calculation of Amount of Condensation

A specific example of finding the amount of condensation formation and calculating the amount of condensation with the condensation calculator 143 on the basis of the result will now be given.

The amount of condensation is calculated from the difference between the condensation formation amount that occurs when exhalation is blown in during measurement, and the natural drying amount by which condensation is reduced through natural drying.

The condensation formation amount is calculated as the product of specific condensation amounts using as a reference a temperature and humidity coefficient that takes outside air temperature, humidity, and so on into account. The temperature and humidity coefficient may be calculated experimentally as follows.

Calculation of Temperature Coefficient

First, the outside air temperature and outside air humidity are divided up and classified into specific ranges. For instance, the outside air temperature is classified into three groups: at least 10° C. and less than 17° C. (group A), at least 17° C. and less than 24° C. (group B), and at least 24° C. (group C). The outside air humidity is classified into two groups: no more than 70% (group 1) and greater than 70% (group 2). These groups may be selected as needed, according to the sensing accuracy required of the device, the environment in which it will be used, and so forth.

Exhalation is then actually blown in to form condensation and the amount thereof is measured under conditions with which condensation is most likely to form in each of the six group combinations (three groups of outside air temperature times two groups of outside air humidity), that is, under an environment in which the outside air temperature is the minimum temperature and the outside air humidity is the maximum humidity.

For example, if the outside air temperature is group A and the outside air humidity is group 1 (hereinafter referred to as group A-1), condensation is formed under an environment with an outside air temperature of 10° C. and a humidity of 70%, and the amount of condensation is measured. In this embodiment, the device is weighed before and after the formation of condensation, and the difference in weight is used as the condensation amount.

Similarly, the amount of condensation is obtained for all six groups, from A-1 to C-2 (outside air temperature group C and outside air humidity group 2), after which these values are used to calculate a temperature and humidity coefficient. The temperature and humidity coefficient is obtained, for example, by using group C-1 (outside air temperature group C and outside air humidity group 1) as a reference, and dividing the amount of condensation of the other groups by the amount of condensation of group C-1. That is, in this case the amount of condensation used in the calculation should be obtained by suitably selecting the average, maximum value, etc., for values obtained in a plurality of measurements. The temperature and humidity coefficient can be calculated in this manner.

Natural Drying Amount

The natural drying amount is calculated as the product of a specific natural drying time and a natural drying coefficient that factors in outside air temperature and humidity and so forth. The natural drying coefficient may be calculated experimentally as follows.

The specific natural drying time is the time elapsed since exhalation was blown in during measurement.

Just as when the temperature and humidity coefficient was calculated above, the outside air temperature and outside air humidity are each divided up and classified into specific ranges. For instance, the outside air temperature is classified into three groups: at least 10° C. and less than 17° C. (group A), at least 17° C. and less than 24° C. (group B), and at least 24° C. (group C). There is only one group for outside air humidity, so there is no classification by outside air humidity. These groups may be selected as needed, according to the sensing accuracy required of the device, the environment in which it will be used, and so forth.

Natural drying is then performed from a state in which a specific amount of condensation was actually formed under the conditions most disadvantageous to the natural drying of condensation in each of the three outside air temperature groups, that is, under an environment in which the outside air temperature was the minimum temperature, until the condensation had disappeared, and how long this takes is measured.

For example, in outside air temperature group A, condensation is naturally dried under an environment in which the outside air temperature is 10° C., and the time it takes for the condensation to disappear (the natural drying time) is measured. That the condensation had disappeared was confirmed visually in this embodiment, but it may instead be confirmed by comparing the weight prior to the formation of condensation.

Similarly, the natural drying times are obtained for each of the three groups (A to C), after which these values are used to calculate a natural drying coefficient. The natural drying coefficient is a value obtained by dividing a specific amount of condensation formed during an experiment by the natural drying time for each of the groups. In this case, the natural drying time used in the calculation may be obtained by suitably selecting the average, maximum value, etc., for values obtained in a plurality of measurements. The natural drying coefficient can be calculated in this manner.

The amount of condensation may be calculated as above, using the temperature and humidity coefficient and the natural drying coefficient calculated as above.

Specifically, as discussed above, the amount of condensation can be found with the following formula:

condensation amount during previous measurement−natural drying amount (natural drying coefficient×specific natural drying time)+amount of condensation formed during current measurement (temperature and humidity coefficient×specific amount of condensation serving as reference)

Here, the amount of condensation when the condensation amount during the previous measurement is less than the natural drying amount is equal to the amount of condensation formed during the current measurement.

For example, if a temperature of 20° C. is measured by the temperature sensor 50, and a humidity of 65% is measured by the humidity sensor 51, the temperature and humidity at that point fall into group B-1.

In an example in which group C-1 is used as a reference, as mentioned above, the temperature and humidity coefficient at this point is (the amount of condensation at group B-1)÷(the amount of condensation at group C-1). Also, the specific amount of condensation serving as a reference is the amount formed when exhalation is actually blown in under the environmental conditions at which condensation is most likely to occur in group C-1 (24° C., 70%).

Also, the natural drying coefficient is the natural drying coefficient found at outside air temperature group B, and the specific natural drying time is the time elapsed since the exhalation was blown in. The blowing in of the exhalation is detected by the pressure sensor 21.

Drive Time Calculation

Next, the drive time of the piezoelectric pump needed to dry up the condensation is found experimentally, and the drive time determination component 144 of the controller 48 calculates the drive time of the piezoelectric pump on the basis of this result.

The following is a specific example.

The drive time of the piezoelectric pump 44 is calculated as the sum of the drive time coefficient that factors in outside air temperature and humidity and so forth, the specific drive time serving as a reference, and the above-mentioned condensation amount. The drive time coefficient may be calculated experimentally as follows.

The specific drive time is the length of time in which a condensation amount per unit of weight can be dried up in the group serving as the reference.

First, the outside air temperature and outside air humidity are each divided up and classified into specific ranges. For instance, the outside air temperature is classified into three groups: at least 10° C. and less than 17° C. (group A), at least 17° C. and less than 24° C. (group B), and at least 24° C. (group C). The outside air humidity is classified into two groups: no more than 70% (group 1) and greater than 70% (group 2). These groups may be selected as needed, according to the sensing accuracy required of the device, the environment in which it will be used, and so forth.

The piezoelectric pump is then actually driven and the drying time is measured under the conditions most disadvantageous to the natural drying of condensation in each of the six group combinations (three groups of outside air temperature times two groups of outside air humidity), that is, under an environment in which the outside air temperature is the minimum temperature and the outside air humidity is the maximum humidity.

For example, if the outside air temperature is group A and the outside air humidity is group 1 (hereinafter referred to as group A-1), the piezoelectric pump is driven under an environment with an outside air temperature of 10° C. and a humidity of 70%, and the time it takes for the condensation to disappear (the drying time) is measured. That the condensation had disappeared was confirmed visually in this embodiment, but it may instead be confirmed by comparing the weight prior to the formation of condensation.

Similarly, the drying times are obtained for each of the six groups from A-1 to C-2 (outside air temperature group C and outside air humidity group 2), after which these values are used to calculate a drive time coefficient.

The drive time coefficient is a value obtained, for example, by using group C-1 (outside air temperature group C and outside air humidity group 1) as a reference, and dividing the drying times of the other groups by the drying time of group C-1.

In this case, the drying time used in the calculation should be obtained by suitably selecting the average, maximum value, etc., for values obtained in a plurality of measurements. The drive time coefficient can be calculated in this manner.

The drive time of the piezoelectric pump 44 may be calculated as above, using the drive time coefficient calculated as above.

Specifically, the drive time of the piezoelectric pump 44 is found from the drive time coefficient×the specific drive time serving as a reference×the above-mentioned condensation amount.

For instance, at a temperature of 20 degrees and a humidity of 65%, the temperature and humidity correspond to group B-1. Therefore, the drive time coefficient is (drying time for group B-1)÷(drying time for group C-1). The specific drive time serving as a reference is the length of time in which a condensation amount per unit of weight can be dried up in the group C-1 serving as the reference.

Once the drive time of the piezoelectric pump 44 has been found as above, the execution component 146 of the drying mode controller 140 closes the valve holes 35 and 38 of the input gas switching device 31 shown in FIG. 6 with the drive valves 36 and 39, and drives the drive valve 52 shown in FIG. 4 to open this valve (S505 in FIG. 15). That is, when the drive valve 52 shown in FIG. 4 is open, since the handle component 1 and the tube 2 are linked to the piezoelectric pump 44 via the upstream part of the flow regulator 22 by the bypass 53, if the piezoelectric pump 44 is driven, outside air is discharged through the handle component 1, the tube 2, the upstream part of the flow regulator 22, and the piezoelectric pump 44 to outside the measuring device main body 3.

That is, the exhalation measuring device in this embodiment is configured so that the handle component 1 and the tube 2 are connected to the piezoelectric pump 44, bypassing the chamber 23, during execution of the drying mode.

As a result, any condensation that has formed inside the tube 2 will be dried up by the above-mentioned outside air flow. This drive of the piezoelectric pump 44 is continued for the above-mentioned pump drive time, and consequently any condensation that has formed inside the tube 2 is dried up by the above-mentioned outside air flow (S506 and S507 in FIG. 15). When this drive time has elapsed, the drive valve 52 is closed, the valve hole 35 of the input gas switching device 31 is open, and the valve hole 38 is closed (S508 in FIG. 15).

The above concludes the drying mode (S508 in FIG. 15), and operation of the measuring device main body 3 is ended (S9 in FIG. 10 and S509 in FIG. 15).

Embodiment 2

Figure 16:
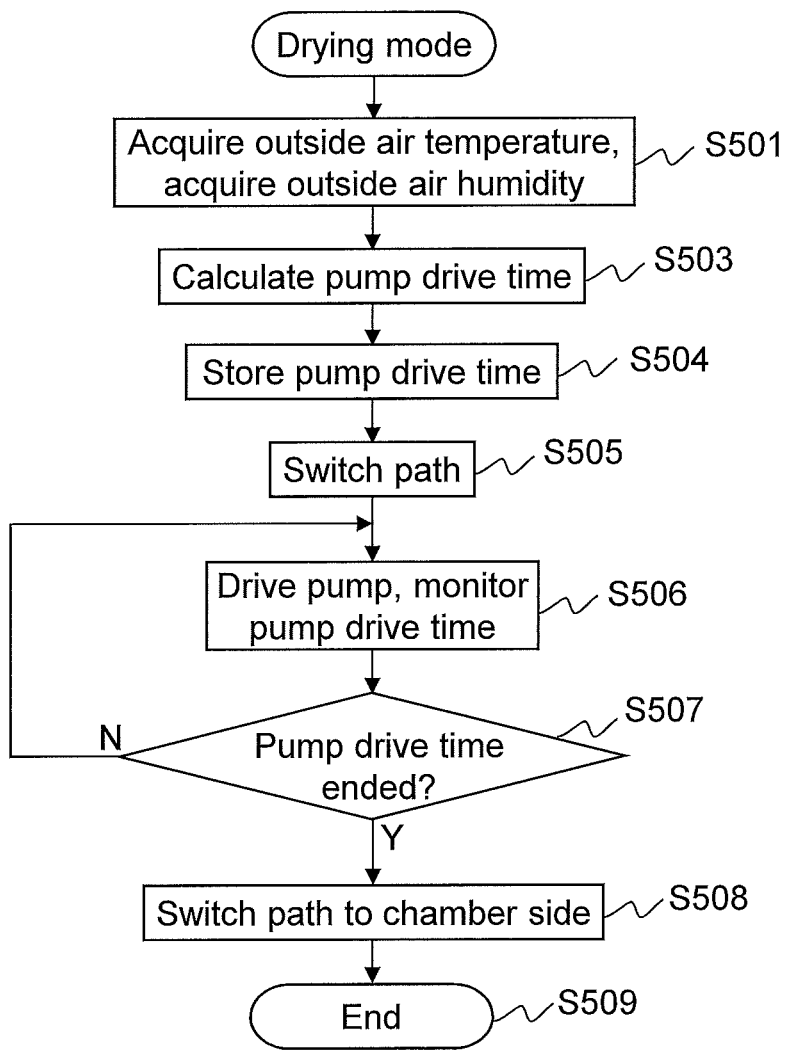
FIG. 16 is an operation flowchart of the exhalation measuring device in Embodiment 2 of the present invention.

FIG. 16 is a flowchart of the method for controlling an exhalation measuring device in Embodiment 2 of the present invention. In Embodiment 1 above, the piezoelectric pump 44 is driven to dry the inside of the tube 2 when the outside air temperature sensed by the temperature sensor 50 dropped to 30 degrees or below, for example, but in Embodiment 2 the drying mode is executed every time measurement ends, regardless of the outside air temperature.

More specifically, during execution of the drying mode, first the temperature acquisition component 141 of the drying mode controller 140 acquires the outside air temperature measured by the temperature sensor 50, and the humidity acquisition component 142 of the drying mode controller 140 acquires the outside air humidity measured by the humidity sensor 51 (S501 in FIG. 16).

Since more condensation is formed when the outside air temperature is low, the condensation calculator 143 of the drying mode controller 140 calculates the amount of condensation from the outside air temperature. Next, the drive time determination component 144 calculates how long to operate the piezoelectric pump 44 to allow outside air to flow into the tube 2 from the handle component 1 in order to dry up this condensation. The humidity measured by the humidity sensor 51 is also taken into account in this calculation.

That is, if the humidity of the outside air flowing from the handle component 1 into the tube 2 is high (higher than 70%, for instance), the drive time of the piezoelectric pump 44 is determined (S503 in FIG. 16) so as to lengthen the drive time of the piezoelectric pump 44 set on the basis of the outside air temperature (to 1.5 times, for instance), and this drive time is stored in the memory 49 (S504 in FIG. 16).

Once this state is reached, the execution component 146 of the drying mode controller 140 closes the valve holes 35 and 38 of the input gas switching device 31 shown in FIG. 6 with the drive valves 36 and 39, and drives the drive valve 52 shown in FIG. 4 to create an open state (S505 in FIG. 16). That is, when the drive valve 52 shown in FIG. 4 is open, since the handle component 1 and the tube 2 are linked to the piezoelectric pump 44 via the upstream part of the flow regulator 22 by the bypass 53, if the piezoelectric pump 44 is driven, outside air is discharged through the handle component 1, the tube 2, the upstream part of the flow regulator 22, and the piezoelectric pump 44 to outside the measuring device main body 3. As a result, any condensation that has formed inside the tube 2 will be dried up by the above-mentioned outside air flow. This drive of the piezoelectric pump 44 is continued for the above-mentioned pump drive time, and consequently any condensation that has formed inside the tube 2 is dried up by the above-mentioned outside air flow (S506 and S507 in FIG. 16). When this drive time has elapsed, the drive valve 52 is closed, the valve hole 35 of the input gas switching device 31 is open, and the valve hole 38 is closed (S508 in FIG. 16).

The above concludes the drying mode (S8 in FIG. 10), and operation of the measuring device main body 3 is ended (S509 in FIG. 16).

Main Features (1)

As discussed above, the exhalation measuring devices in Embodiments 1 and 2 pertaining to the present invention comprise the handle component 1, the chamber 23, the piezoelectric pump 44 (an example of a pump), and the drying mode controller 140. Exhalation is blown into the handle component 1. The exhalation that is blown in is temporarily held in the chamber 23. The piezoelectric pump 44 supplies the exhalation held in the chamber 23 to the measurement component 45. The drying mode controller 140 drives the piezoelectric pump 44 after measurement of the exhalation by the measurement component 45, and executes a drying mode in which outside air is drawn in from the handle component 1.

This improves sensing accuracy.

Specifically, the controller 48 is configured to drive the piezoelectric pump 44 after the measurement of the exhalation by the measurement component 45, and execute a drying mode in which outside air is drawn in from the handle component 1, so the drying mode is executed after measurement, and as a result less condensation accumulates in the area downstream from the handle component 1, and this improves sensing accuracy.

(2)

With the exhalation measuring device in this embodiment, the drying mode controller 140 has the temperature acquisition component 141 that acquires a measurement value from the temperature sensor 50. The drying mode controller 140 executes the drying mode on the basis of the measurement value of the temperature sensor 50.

Consequently, the drying mode can be executed properly for an amount of condensation that varies with the temperature.

(3)

With the exhalation measuring device in this embodiment, the drying mode controller 140 has the execution determination component 145 that determines whether or not the measurement value acquired from the temperature sensor 50 is lower than a specific value. If the measurement value from the temperature sensor 50 is lower than this specific value, the drying mode is executed.

Since extremely little condensation is formed when the outside air temperature is at or above a certain level (such as 30° C.), there is no need to execute the drying mode in that case. Specifically, executing the unnecessary drying mode can be eliminated by determining whether or not the temperature is below the specific level.

(4)

With the exhalation measuring device in this embodiment, the temperature sensor 50 measures the outside air temperature. Consequently, the drying mode can be executed on the basis of the outside air temperature.

(5)

With the exhalation measuring device in this embodiment, the drying mode controller 140 has the temperature acquisition component 141, the condensation calculator 143, and the drive time determination component 144. The temperature acquisition component 141 acquires a measurement value from the temperature sensor 50. The condensation calculator 143 calculates the amount of condensation inside the tube 2 on the basis of the measurement value from the temperature sensor 50. The drive time determination component 144 determines the drive time of the piezoelectric pump 44 during which outside air will be drawn in from the handle component 1, according to the calculated amount of condensation.

Consequently, the execution time of the drying mode can be controlled on the basis of the amount of condensation. Accordingly, it takes less time until control is ended after the concentration has been displayed, which improves user convenience.

(6)

With the exhalation measuring device in this embodiment, the drying mode controller 140 has the temperature acquisition component 141 and the humidity acquisition component 142. The temperature acquisition component 141 acquires measurement values from the temperature sensor 50. The humidity acquisition component 142 acquires measurement values from the humidity sensor 51. The drying mode controller 140 executes the drying mode on the basis of the measurement results from the temperature sensor 50 and the humidity sensor 51.

This allows the drying mode to be properly executed for the amount of condensation, which varies with the temperature and humidity.

(7)

With the exhalation measuring device in this embodiment, the drying mode controller 140 has the execution determination component 145 that executes the drying mode when the measurement value of the temperature sensor 50 is below a specific level. The drying mode controller 140 lengths the duration of the drying mode when the measurement value of the humidity sensor 51 is above a specific level.

Since extremely little condensation is formed when the outside air temperature is at or above a certain level (such as 30° C.), there is no need to execute the drying mode in that case. Specifically, executing the unnecessary drying mode can be eliminated by determining whether or not the temperature is below the specific level.

Also, the drying mode can be properly executed for an amount of condensation that varies with humidity.

(8)

With the exhalation measuring device in this embodiment, the temperature sensor 50 measures the temperature of the outside air, and the humidity sensor 51 measures the humidity of the outside air. This allows the drying mode to be executed on the basis of the outside air temperature and humidity.

(9)

With the exhalation measuring device in this embodiment, the drying mode controller 140 has the temperature acquisition component 141, the humidity acquisition component 142, the condensation calculator 143, and the drive time determination component 144. The temperature acquisition component 141 acquires the measurement value from the temperature sensor 50. The humidity acquisition component 142 acquires the measurement value from the humidity sensor 51. The condensation calculator 143 calculates the amount of condensation inside the tube 2 on the basis of the measurement values of the temperature sensor 50 and the humidity sensor 51. The drive time determination component 144 determines how long to drive the piezoelectric pump 44 to draw in outside air from the handle component 1, according to the calculated amount of condensation.

Consequently, the drying mode execution time can be controlled on the basis of the condensation amount, which varies with the temperature and humidity. Therefore, it will take less time until control is ended after the concentration has been displayed, and this improves user convenience.

(10)

With the exhalation measuring device in this embodiment, the drying mode controller 140 connects the tube 2 to the piezoelectric pump 44, bypassing the chamber 23, during drying mode execution. Consequently, condensation can be discharged to the outside without going through the chamber 23, etc.

(11)

The method for controlling an exhalation measuring device in this embodiment is a method for controlling an exhalation measuring device comprising the handle component 1, the chamber 23, and the piezoelectric pump 44, said method comprising steps S7 (an example of a measurement step) and S8 (an example of a drying mode execution step). Exhalation is blown into the handle component 1. The exhalation that is blown in is temporarily held in the chamber 23. The piezoelectric pump 44 supplies the exhalation held in the chamber 23 to the measurement component 45. Step S7 (an example of a measurement step) involves using the measurement component 45 to measure the exhalation supplied by the piezoelectric pump 44. Step S8 (an example of a drying mode execution step) involves driving the piezoelectric pump 44 to execute a drying mode in which outside air is drawn in through the handle component 1, after step S7 (an example of a measurement step).

Consequently, the drying mode is executed after measurement, and as a result less condensation accumulates in the area downstream from the handle component 1, and this improves sensing accuracy.

(12)

With the method for controlling an exhalation measuring device in this embodiment, S8 (an example of a drying mode execution step) has steps S501 (an example of a temperature acquisition step and a humidity acquisition step) and S503 (an example of a pump drive time calculation step). S503 (an example of a pump drive time calculation step) involves calculating the amount of condensation inside the tube 2 on the basis of the measurement result from S501 (an example of a temperature acquisition step and a humidity acquisition step), and determining how long to operate the piezoelectric pump 44 in order to draw in outside air, according to the calculated amount of condensation.

Consequently, the drying mode execution time can be controlled on the basis of the amount of condensation, which varies with temperature and humidity.

(13)

With the method for controlling an exhalation measuring device in this embodiment, S8 (an example of a drying mode execution step) has S502 (an example of a temperature determination step) and S506 and S507 (examples of an operation step). S502 (an example of a temperature determination step) involves determining that the measurement result in S501 (an example of a temperature acquisition step) is lower than a specific value. S506 and S507 (examples of an operation step) involve operating the piezoelectric pump 44 in order to draw in outside air on the basis of the determination result of S502 (an example of a temperature determination step).

Thus determining whether or not the temperature is lower than a specific value eliminates excusing the unnecessary drying mode.

(14)

With the method for controlling an exhalation measuring device in this embodiment, S8 (an example of a drying mode execution step) further has S505 (an example of a path switching step).

S505 (an example of a path switching step) switches the flow path so as to bypass the chamber 23 in supplying the exhalation that is drawn in to the piezoelectric pump 44. This allows condensation to be discharged to the outside without going through the chamber 23, etc.

Other Embodiments (A)

The piezoelectric pump 44 was used in the above embodiment, but some other pump that is driven by a motor may be used instead.

(B)

In Embodiments 1 and 2 above, the description focused on condensation formed inside the tube 2, where most of the condensation forms and where the measurement result is assumed to be affected, but it is also conceivable that condensation will form elsewhere, such as in the handle component 1, the flow regulator 22, the chamber 23, etc.

Therefore, the configuration may be such that drying of the handle component 1, the flow regulator 22, the chamber 23, and so forth is further performed with outside air drawn in through the handle component 1 and the tube 2.

In this case, the amount of condensation formed may be obtained by experimentally finding the relation between the amount of condensation formed and the outside air temperature in the handle component 1, the flow regulator 22, the chamber 23, and so forth, in addition to the conditions set forth in Embodiments 1 and 2 above, and the controller 48 may calculate the amount of condensation on the basis of this result. This allows the condensation amount to be calculated more accurately.

(C)

With the exhalation measuring devices in Embodiments 1 and 2 above, the temperature sensor 50 and the humidity sensor 51 are provided. But the temperature sensor 50 and the humidity sensor 51 may not be provided, and the user may input the temperature and humidity to the exhalation measuring device. In other words, what matters is that the exhalation measuring device can acquire the values for temperature and humidity.

(D)

Also, the exhalation measuring devices in Embodiments 1 and 2 above has the temperature acquisition component 141 and the humidity acquisition component 142, but may have only the temperature acquisition component 141. In this case, the drying mode is executed on the basis of temperature.

(E)

With the exhalation measuring devices in Embodiments 1 and 2 above, the valve holes 35 and 38 of the input gas switching device 31 are closed by the drive valves 36 and 39 and the drive valve 52 is opened in executing the drying mode, but this is not the only option, and instead the valve hole 24 of the flow regulator 22 may be closed by the drive valve 25, and the drive valve 52 opened.

(F)

Also, in Embodiments 1 and 2 above, a configuration is described in which exhalation is blown into the chamber 23 through the handle component 1 and the tube 2, but the configuration of the present invention is not limited to this. That is, the configuration may be, for example, such that the handle component 1 and the tube 2 are not provided, and exhalation is blown into the chamber 23.

Here again, as discussed above, the drying mode controller 140 executes the drying mode by driving the piezoelectric pump 44 after the measurement of exhalation by the measurement component 45, which allows the chamber 23, etc., to be dried by outside air drawn into the chamber 23. As a result, there will be less accumulation of condensation in the chamber 23, etc., so sensing accuracy can be improved.

Specifically, an exhalation measuring device with this configuration comprises the chamber 23, the piezoelectric pump 44 (an example of a pump), and the drying mode controller 140. The exhalation that is blown in is temporarily held in the chamber 23. The piezoelectric pump 44 supplies the exhalation held in the chamber 23 to the measurement component 45. The drying mode controller 140 executes the drying mode in which outside air is drawn in by driving the piezoelectric pump 44 after the measurement of exhalation by the measurement component 45.

Also, the drying mode controller 140 has the condensation calculator 143 and the drive time determination component 144. The condensation calculator 143 calculates the amount of condensation inside the exhalation measuring device (inside the measuring device main body 3) on the basis of the measurement values from the temperature sensor 50 and the humidity sensor 51. The drive time of the piezoelectric pump 44 during which outside air is drawn in is determined according to the calculated amount of condensation.

Also, the amount of condensation in the exhalation measuring device may be calculated on the basis of just the temperature from the temperature sensor 50. In this case, the condensation calculator 143 of the drying mode controller 140 calculates the amount of condensation in the exhalation measuring device on the basis of the measurement value from the temperature sensor 50.

INDUSTRIAL APPLICABILITY

The exhalation measuring device of certain implementations of the present invention has the effect of improving sensing accuracy, and is expected to find use in exhalation measuring devices used in performing asthma detection, pulmonary function sensing, and so forth.

The invention claimed is:

1. An exhalation measuring device, comprising:
a handle component into which exhalation is blown;
a chamber into which the exhalation is supplied from the handle component through a tube and temporarily held;
a pump for supplying the exhalation held in the chamber to a measurement component;
a controller for controlling an operation of the pump;
a temperature sensor that is connected to the controller;
a bypass that connects the tube to the pump by bypassing the chamber; and
a valve that opens and closes the bypass, and
wherein the controller:
determines whether or not to perform a drying mode for removing condensation inside the tube, on the basis of temperature acquired by the temperature sensor, after the measurement of exhalation by the measurement component,
drives the pump to draw in outside air from the handle component and supply it to the tube when it has been determined to perform the drying mode, and
controls the valve in the drying mode so that the chamber is bypassed, and drives the pump to draw in outside air from the handle component and supply it to the tube.

2. The exhalation measuring device according to claim 1, wherein the controller determines to perform the drying mode when the temperature acquired by the temperature sensor is at or below a specific value.

3. The exhalation measuring device according to claim 1, wherein the controller determines drive time for the pump on the basis of the temperature acquired by the temperature sensor.

4. The exhalation measuring device according to claim 1, wherein the controller:
calculates an amount of condensation inside the tube on the basis of the temperature acquired by the temperature sensor, and
determines to perform the drying mode when the calculated amount of condensation exceeds a specific value.

5. The exhalation measuring device according to claim 4, wherein the controller determines drive time for the pump on the basis of the calculated amount of condensation.

6. The exhalation measuring device according to claim 1, wherein the temperature sensor acquires outside air temperature.

7. The exhalation measuring device according to claim 1, further comprising a humidity sensor that is connected to the controller and measures outside air humidity,
wherein the controller determines whether or not to perform the drying mode on the basis of the outside temperature acquired by the temperature sensor and the outside air humidity acquired by the humidity sensor.

8. The exhalation measuring device according to claim 7, wherein, when the outside air humidity acquired by the humidity sensor is higher than specific value, the controller lengthens the drive time for the pump over that when the humidity is lower than this specific value.

9. The exhalation measuring device according to claim 7, wherein the controller:
calculates an amount of condensation inside the tube on the basis of the temperature acquired by the temperature sensor and the outside air humidity acquired by the humidity sensor, and
determines a drive time of the pump on the basis of a calculated amount of condensation.

10. A method for controlling an exhalation measuring device that comprises:
a handle component into which exhalation is blown;
a chamber into which the exhalation is supplied from the handle component through a tube and temporarily held;
a pump for supplying the exhalation held in the chamber to a measurement component;
a controller for controlling an operation of the pump; and
a temperature sensor that is connected to the controller,
said method comprising:
a measurement step of using the measurement component to measure the exhalation supplied by the pump;
a determination step of determining whether or not to perform a drying mode in which condensation inside the tube is dried up, on the basis of temperature acquired by the temperature sensor; and
a drying mode execution step of driving the pump to draw in outside air from the handle component and supply it to the tube, wherein the drying mode execution step further includes a path switching step of switching a path so that the tube is connected to the pump, bypassing the chamber.

11. The method for controlling an exhalation measuring device according to claim 10, further comprising a humidity sensor that is connected to the controller and measures outside air humidity, wherein the determination step includes:

a condensation amount calculation step of calculating an amount of condensation inside the tube on the basis of temperature acquired by the temperature sensor and the outside air humidity acquired by the humidity sensor; and a pump drive time calculation step of determining drive time for the pump on the basis of the calculated amount of condensation.

* * * * *